(12) United States Patent
Wolfe et al.

(10) Patent No.: US 12,064,449 B2
(45) Date of Patent: Aug. 20, 2024

(54) COMPOSITIONS AND METHODS FOR IMPROVEMENT OF IRON METABOLISM AND GUT MICROBIOME HEALTH

(71) Applicant: Sidero Bioscience, LLC, Hummelstown, PA (US)

(72) Inventors: Darren Wolfe, Cincinnati, OH (US); James Connor, Hershey, PA (US)

(73) Assignee: SIDERO BIOSCIENCE, LLC, Hummelstown, PA (US)

(*) Notice: Subject to any disclaimer, the term of this patent is extended or adjusted under 35 U.S.C. 154(b) by 860 days.

(21) Appl. No.: 16/972,090

(22) PCT Filed: Jun. 4, 2019

(86) PCT No.: PCT/US2019/035437
§ 371 (c)(1),
(2) Date: Dec. 4, 2020

(87) PCT Pub. No.: WO2019/236611
PCT Pub. Date: Dec. 12, 2019

(65) Prior Publication Data
US 2021/0220396 A1   Jul. 22, 2021

Related U.S. Application Data

(60) Provisional application No. 62/680,238, filed on Jun. 4, 2018.

(51) Int. Cl.
| | | |
|---|---|---|
| A61K 33/26 | (2006.01) | |
| A23L 33/00 | (2016.01) | |
| A23L 33/14 | (2016.01) | |
| A23L 33/165 | (2016.01) | |
| A23L 33/17 | (2016.01) | |
| A61K 35/74 | (2015.01) | |
| A61K 36/06 | (2006.01) | |

(52) U.S. Cl.
CPC ............ *A61K 33/26* (2013.01); *A23L 33/14* (2016.08); *A23L 33/165* (2016.08); *A23L 33/17* (2016.08); *A23L 33/30* (2016.08); *A61K 35/74* (2013.01); *A61K 36/06* (2013.01)

(58) Field of Classification Search
None
See application file for complete search history.

(56) References Cited

U.S. PATENT DOCUMENTS

| | | |
|---|---|---|
| 8,071,542 B2 | 12/2011 | Connor et al. |
| 8,778,878 B2 | 7/2014 | Connor et al. |
| 9,687,513 B2 | 6/2017 | Alenfall et al. |
| 2004/0186048 A1 | 9/2004 | Broyles et al. |
| 2006/0116349 A1 | 6/2006 | Helenek et al. |
| 2007/0160658 A1 | 7/2007 | Connor et al. |
| 2011/0132498 A1 | 6/2011 | Nojima et al. |
| 2014/0322162 A1 | 10/2014 | Connor et al. |

FOREIGN PATENT DOCUMENTS

| | | |
|---|---|---|
| CN | 1257931 | 6/2009 |
| WO | 2019/236611 | 12/2019 |

OTHER PUBLICATIONS

Beard et al., Purified Ferritin and Soybean Meal Can be Sources of Iron for Treating Iron Deficiency in Rats. Human and Clinical Nutrition, (1995), pp. 154-160.
Fisher et al., "Ferritin: a novel mechanism for delivery of iron to the brain and other organs". Am. J. Physiol Cell Physiol (2007) vol. 293: pp. C641-C649.
Hulet et al., "Oligodendrocyte Progenitor Cells Internalize Ferritin via Clathrin-Dependent Receptor Mediated Endocytosis". J. Neurosci. Res., (2000) vol. 61, pp. 52-60 (Abstract Only).
Roncagliolo et al., "Evidence of Altered Central Nervous System Development in Infants with Iron Deficiency Anemia at 6 mo: Delayed Maturation of Auditory Brainstem Responses". Am. J. Clin. Nutr., (1998), vol. 68, pp. 683-690.
Korcok et al., "Development of Probiotic Formulation for the Treatment of Iron Deficiency Anemia". Chemical & Pharmaceutical Bulletin (2018) vol. 66, No. 4, pp. 347-352.
Seo et al., Enhanced expression and functional characterization of the human ferritin H- and L-chain genes in *Saccharomyces cerevisiae*, Appl. Microbiol Biotechnol (2003) vol. 63: pp. 57-63.
Mahoney et al., Potential of the Rat as a Model for Predicting Iron Bioavailability for Humans. Nutrition Research, (1984) vol. 4, pp. 913-922.
Chang et al., Recovery from iron deficiency in rats by the intake of recombinant yeast producing human H-ferritin. Nutrition 21 (2005) pp. 520-524.

*Primary Examiner* — Robert A Wax
*Assistant Examiner* — Quanglong N Truong
(74) *Attorney, Agent, or Firm* — Alicia M. Passerin; Leech Tishman Fuscaldo & Lampl

(57) ABSTRACT

Disclosed is a composition comprising a microbe expressing ferritin. The composition also comprises elemental iron in an amount of at least 3% by weight on a dry matter basis of the microbe expressing ferritin and the elemental iron. Also disclosed are ingestibles, dietary supplements, and pharmaceutical compositions comprising the composition. Also disclosed are methods for treating a subject comprising administering the composition to the subject. Also disclosed are methods of altering the composition of the gut bacterial microbiome in a subject, the method comprising administering the composition to the subject.

28 Claims, 37 Drawing Sheets

Figure 1 a

MTTASTSQVRQNYHQDSEAAINRQINLELYASYVYLSMSYYFDRDDVALKNFAKYFL
HQSHEEREHAEKLMKLQNQRGGRIFLQDIKKPDCDDWESGLNAMECALHLEKNVNQS
LLELHKLATDKNDPHLCDFIETHYLNEQVKAIKELGDHVTNLRKMGAPESGLAEYLF
DKHTLGDSDNES

Figure 1 b

ATGGCTGATATC
GGATCCATACATATGACGACCGCGTCCACCTCGCAGGTGCGCCAGAACTACCACCAG
GACTCAGAGGCCGCCATCAACCGCCAGATCAACCTGGAGCTCTACGCCTCCTACGTT
TACCTGTCCATGTCTTACTACTTTGACCGCGATGATGTGGCTTTGAAGAACTTTGCC
AAATACTTTCTTCACCAATCTCATGAGGAGAGGGAACATGCTGAGAAACTGATGAAG
CTGCAGAACCAACGAGGTGGCCGAATCTTCCTTCAGGATATCAAGAAACCAGACTGT
GATGACTGGGAGAGCGGGCTGAATGCAATGGAGTGTGCATTACATTTGGAAAAAAAT
GTGAATCAGTCACTACTGGAACTGCACAAACTGGCCACTGACAAAAATGACCCCCAT
TTGTGTGACTTCATTGAGACACATTACCTGAATGAGCAGGTGAAAGCCATCAAAGAA
TTGGGTGACCACGTGACCAACTTGCGCAAGATGGGAGCGCCCGAATCTGGCTTGGCG
GAATATCTCTTTGACAAGCACACCCTGGGAGACAGTGATAATGAAAGCTAACCTAGG
CACCTCGAG

*Study Calendar*

| | Visit 1 Week -4 | Visit 2 Week 0 | Visit 3 Week 1 | Visit 4 Week 2 | Visit 5 Week 3 | Visit 6 Week 4 | Visit 7 Week 6 | Visit 8 Week 8 | Visit 9 Week 10 |
|---|---|---|---|---|---|---|---|---|---|
| | Screen[1] | Enroll | Follow-up | Increase Intake | Follow-up | Follow-up | Follow-up | Follow-up | End of Study |
| Intake Level | | Start 1.5 g/d | 1.5 g/d | Start 3.0 g/d | 3.0 g/d | 3.0 g/d | 3.0 g/d | Stop 3.0 g/d | |
| Medical History | X | | | | | | | | |
| Limited Physical[2] | X | | | | | | | | |
| Pregnancy Testing[3] | X | | | | | | | | |
| Adverse Events[4] | | X | X | X | X | X | X | X | X |
| Concomitant Medications[5] | X | X | X | X | X | X | X | X | X |
| Diet/Menses Review[6] | X | X | X | X | X | X | X | X | X |
| Vital Signs & Weight[7] | X | X | X | X | X | X | X | X | X |
| Local Labs[8] | X | X | X | X | X | X | X | X | X |
| Health Surveys[9] | X | X | X | X | X | X | X | X | X |
| Stool Sampling[10] | X | | | X | | X | | X | X |

FIG. 5

*Footnotes*
1) Consumption of iron supplements was stopped, or iron containing multivitamins were switched to vitamins not containing iron, for at least four weeks before screening. Screening took place up to four weeks prior to enrollment. The time between screening and enrollment was minimal as practical.
2) Limited physical exam by a licensed physician or advanced practice nurse targeting the circulatory and digestive systems
3) Urine was collected from all female participants for pregnancy testing.
4) AE review began at the time of enrollment and continued until Week 10/Visit 9 and was completed by clinical personnel at every visit.
5) Current concomitant medication and dose capture, including compliance with Composition A, began at the time of screening (30 days prior) and continued until Week 10/Visit 9 and was completed by clinical personnel at every visit.
6) General questioning about dietary changes and menses status and regularity since last contact was completed by clinical personnel at every visit.
7) Vital signs included blood pressure, heart rate, temperature and weight.
8) Local labs included serum iron, TIBC, serum ferritin, C-reactive protein, CBC with differential, and CMP
9) Health Survey questionnaires were reviewed for completeness, unreported AEs or discrepancies in the subject's health record, and collected by clinical personnel at every visit.
10) Screening stool sample was collected as close to the enrollment visit as possible. Week 8 stool sample was collected just prior to discontinuation of Composition A. All other stool samples were collected just prior to the coinciding visit.

FIG. 5 Continued

FACIT Fatigue Scale (Version 4)

Please circle or mark one number per line to indicate your response as it applies to the past 7 days.

|  | Not at all | A little bit | Some-what | Quite a bit | Very much |
|---|---|---|---|---|---|
| I feel fatigued | 0 | 1 | 2 | 3 | 4 |
| I feel weak all over | 0 | 1 | 2 | 3 | 4 |
| I feel listless ("washed out") | 0 | 1 | 2 | 3 | 4 |
| I feel tired | 0 | 1 | 2 | 3 | 4 |
| I have trouble starting things because I am tired | 0 | 1 | 2 | 3 | 4 |
| I have trouble finishing things because I am tired | 0 | 1 | 2 | 3 | 4 |
| I have energy | 0 | 1 | 2 | 3 | 4 |
| I am able to do my usual activities | 0 | 1 | 2 | 3 | 4 |
| I need to sleep during the day | 0 | 1 | 2 | 3 | 4 |
| I am too tired to eat | 0 | 1 | 2 | 3 | 4 |
| I need help doing my usual activities | 0 | 1 | 2 | 3 | 4 |
| I am frustrated by being too tired to do the things I want to do | 0 | 1 | 2 | 3 | 4 |
| I have to limit my social activity because I am tired | 0 | 1 | 2 | 3 | 4 |

FIG. 9

 

RAND > RAND Health Care > Surveys > RAND Medical Outcomes Study > 36-Item Short Form Survey (SF-36) >

36-Item Short Form Survey Instrument (SF-36)

RAND 36-Item Health Survey 1.0 Questionnaire Items

Choose one option for each questionnaire item.

1. In general, would you say your health is:

○ 1 - Excellent

○ 2 - Very good

○ 3 - Good

○ 4 - Fair

○ 5 - Poor

2. Compared to one year ago, how would you rate your health in general now?

○ 1 - Much better now than one year ago

○ 2 - Somewhat better now than one year ago

○ 3 - About the same

○ 4 - Somewhat worse now than one year ago

○ 5 - Much worse now than one year ago

FIG. 11A

The following items are about activities you might do during a typical day. Does your health now limit you in these activities? If so, how much?

|  | Yes, limited a lot | Yes, limited a little | No, not limited at all |
|---|---|---|---|
| 3. Vigorous activities, such as running, lifting heavy objects, participating in strenuous sports | ◯ 1 | ◯ 2 | ◯ 3 |
| 4. Moderate activities, such as moving a table, pushing a vacuum cleaner, bowling, or playing golf | ◯ 1 | ◯ 2 | ◯ 3 |
| 5. Lifting or carrying groceries | ◯ 1 | ◯ 2 | ◯ 3 |
| 6. Climbing several flights of stairs | ◯ 1 | ◯ 2 | ◯ 3 |
| 7. Climbing one flight of stairs | ◯ 1 | ◯ 2 | ◯ 3 |
| 8. Bending, kneeling, or stooping | ◯ 1 | ◯ 2 | ◯ 3 |
| 9. Walking more than a mile | ◯ 1 | ◯ 2 | ◯ 3 |
| 10. Walking several blocks | ◯ 1 | ◯ 2 | ◯ 3 |
| 11. Walking one block | ◯ 1 | ◯ 2 | ◯ 3 |
| 12. Bathing or dressing yourself | ◯ 1 | ◯ 2 | ◯ 3 |

FIG. 11B

During the past 4 weeks, have you had any of the following problems with your work or other regular daily activities as a result of your physical health?

|  | Yes | No |
|---|---|---|
| 13. Cut down the amount of time you spent on work or other activities | 1 | 2 |
| 14. Accomplished less than you would like | 1 | 2 |
| 15. Were limited in the kind of work or other activities | 1 | 2 |
| 16. Had difficulty performing the work or other activities (for example, it took extra effort) | 1 | 2 |

During the past 4 weeks, have you had any of the following problems with your work or other regular daily activities as a result of any emotional problems (such as feeling depressed or anxious)?

|  | Yes | No |
|---|---|---|
| 17. Cut down the amount of time you spent on work or other activities | 1 | 2 |
| 18. Accomplished less than you would like | 1 | 2 |
| 19. Didn't do work or other activities as carefully as usual | 1 | 2 |

20. During the past 4 weeks, to what extent has your physical health or emotional problems interfered with your normal social activities with family, friends, neighbors, or groups?

○ 1 - Not at all

○ 2 - Slightly

○ 3 - Moderately

○ 4 - Quite a bit

○ 5 - Extremely

FIG. 11C

21. How much bodily pain have you had during the past 4 weeks?

○ 1 - None

○ 2 - Very mild

○ 3 - Mild

○ 4 - Moderate

○ 5 - Severe

○ 6 - Very severe

22. During the past 4 weeks, how much did pain interfere with your normal work (including both work outside the home and housework)?

○ 1 - Not at all

○ 2 - A little bit

○ 3 - Moderately

○ 4 - Quite a bit

○ 5 - Extremely

FIG. 11D

These questions are about how you feel and how things have been with you during the past 4 weeks. For each question, please give the one answer that comes closest to the way you have been feeling.

How much of the time during the past 4 weeks...

|  | All of the time | Most of the time | A good bit of the time | Some of the time | A little of the time | None of the time |
|---|---|---|---|---|---|---|
| 23. Did you feel full of pep? | 1 | 2 | 3 | 4 | 5 | 6 |
| 24. Have you been a very nervous person? | 1 | 2 | 3 | 4 | 5 | 6 |
| 25. Have you felt so down in the dumps that nothing could cheer you up? | 1 | 2 | 3 | 4 | 5 | 6 |
| 26. Have you felt calm and peaceful? | 1 | 2 | 3 | 4 | 5 | 6 |
| 27. Did you have a lot of energy? | 1 | 2 | 3 | 4 | 5 | 6 |
| 28. Have you felt downhearted and blue? | 1 | 2 | 3 | 4 | 5 | 6 |
| 29. Did you feel worn out? | 1 | 2 | 3 | 4 | 5 | 6 |
| 30. Have you been a happy person? | 1 | 2 | 3 | 4 | 5 | 6 |
| 31. Did you feel tired? | 1 | 2 | 3 | 4 | 5 | 6 |

32. During the past 4 weeks, how much of the time has your physical health or emotional problems interfered with your social activities (like visiting with friends, relatives, etc.)?

○ 1 - All of the time

○ 2 - Most of the time

○ 3 - Some of the time

○ 4 - A little of the time

○ 5 - None of the time

FIG. 11E

How TRUE or FALSE is each of the following statements for you.

|  | Definitely true | Mostly true | Don't know | Mostly false | Definitely false |
|---|---|---|---|---|---|
| 33. I seem to get sick a little easier than other people | ○ 1 | ○ 2 | ○ 3 | ○ 4 | ○ 5 |
| 34. I am as healthy as anybody I know | ○ 1 | ○ 2 | ○ 3 | ○ 4 | ○ 5 |
| 35. I expect my health to get worse | ○ 1 | ○ 2 | ○ 3 | ○ 4 | ○ 5 |
| 36. My health is excellent | ○ 1 | ○ 2 | ○ 3 | ○ 4 | ○ 5 |

ABOUT

The RAND Corporation is a research organization that develops solutions to public policy challenges to help make communities throughout the world safer and more secure, healthier and more prosperous. RAND is nonprofit, nonpartisan, and committed to the public interest.

1776 Main Street
Santa Monica, California 90401-3208

RAND® is a registered trademark. Copyright © 1994-2016 RAND Corporation.

FIG. 11F

Please record any symptoms you may have had today *(tick one box for each symptom experienced)*
Absent     *I did not have this symptom at all*
Mild     *I had this symptom occasionally, but it did not really bother me*
Moderate     *I had this symptom often, it bothered me quite a bit*
Severe     *I had this symptom very often, it bothered me a great deal*

| | Absent | Mild | Moderate | Severe |
|---|---|---|---|---|
| Have you felt any nausea (wanting to vomit) today? | ☐ | ☐ | ☐ | ☐ |
| Have you actually vomited today? | ☐ | ☐ | ☐ | ☐ |
| Have you had heartburn (burning in chest) today? | ☐ | ☐ | ☐ | ☐ |
| Have you had abdominal pain today? | ☐ | ☐ | ☐ | ☐ |
| Have you had a headache today? | ☐ | ☐ | ☐ | ☐ |
| Have you been breathless today? | ☐ | ☐ | ☐ | ☐ |
| Have you had diarrhoea today? | ☐ | ☐ | ☐ | ☐ |
| Have you had constipation today? | ☐ | ☐ | ☐ | ☐ |

How many bowel movements have you had today? *(Specify)* ☐☐
Is this normal for you?     Yes ☐     No ☐
How many of your bowel movements were black? *(Specify)* ☐☐

Did you take your tablets today? *(If yes, please tick box)*
Morning ☐     Evening ☐
If you did not take either of your tablets, please explain why?

FIG. 14

COMPOSITIONS AND METHODS FOR IMPROVEMENT OF IRON METABOLISM AND GUT MICROBIOME HEALTH

CROSS-REFERENCE

This application claims priority to U.S. Provisional Application No. 62/680,238 entitled "Composition and Method for Treatment of Iron Deficiency" filed on Jun. 4, 2018.

TECHNICAL FIELD

The present disclosure relates to the management of a nutrient deficiency and subsequent symptoms or diseases, as well as management and regulation of gut microbiome.

BACKGROUND

Iron deficiency is the most common and widespread nutritional disorder worldwide, affecting up to two billion people. Iron is one of life's most important nonorganic substances with major roles in oxygen transport, short-term oxygen storage, and energy generation to name a few of its fundamental roles in organismal physiology. Deficiencies in iron absorption or excesses in iron loss leads to non-optimal blood and/or tissue iron levels with a wide variety of symptoms.

Current iron replacement options are plainly inadequate and new strategies are desperately needed for persons with body iron deficiency. Intolerance to oral iron supplementation is common and largely due to problematic GI side effects. In addition, many (actually most) patients with iron deficiency are not responsive to oral iron treatments leaving them iron deficient.

Each individual has a personalized gastrointestinal microbiome (also referred to herein as gut microbiota, intestinal microbiota, microbial flora, gut microbiome) including an estimated 500 to 5000 or more species of bacteria, fungi, viruses, archaea and other microorganisms, up to 100 trillion individual organisms, that reside in the digestive tract, providing a host of useful symbiotic functions, for example, including aiding in digestion, providing nutrition for the colon, producing vitamins, regulating the immune system, assisting in defense against exogenous bacteria, modulating energy metabolism, and the production of metabolites and signaling molecules that act on cells or tissues of the host and/or other microbiota. An imbalance in the microbial flora found in and on the human body is known to be associated with a variety of disease states including gastrointestinal conditions, but also systemic conditions, e.g., allergy, autoimmunity, CNS conditions, obesity, and susceptibility to pathogenic infections. Many of these diseases and disorders are chronic conditions that significantly decrease a patient's quality of life and can be ultimately fatal. In settings of "dysbiosis" or disrupted symbiosis of the gut microbiome, microbiota functions can be lost or deranged, resulting in increased susceptibility to pathogens, include altered metabolic profiles, or induction of proinflammatory signals that can result in local or systemic inflammation or autoimmunity. As such, there is a need in the field of microbiology for a new and useful methods for modulating the microbiome or treating a microbiome dysbiosis.

SUMMARY

Disclosed herein is a composition comprising (a) a microbe expressing ferritin and (b) elemental iron in an amount of at least 3% by weight on a dry matter basis of the microbe expressing ferritin and the elemental iron.

Also disclosed herein is an ingestible comprising (a) a microbe expressing ferritin and (b) elemental iron in an amount of at least 3% by weight on a dry matter basis of the microbe expressing ferritin and the elemental iron.

Also disclosed is a dietary supplement comprising (a) a microbe expressing ferritin and (b) elemental iron in an amount of at least 3% by weight on a dry matter basis of the microbe expressing ferritin and the elemental iron.

Also disclosed is a pharmaceutical composition comprising (a) a microbe expressing ferritin and (b) elemental iron in an amount of at least 3% by weight on a dry matter basis of the microbe expressing ferritin and the elemental iron.

Also disclosed is a method for treating a subject comprising administering to the subject a composition comprising (a) a microbe expressing ferritin and (b) elemental iron in an amount of at least 3% by weight on a dry matter basis of the microbe expressing ferritin and the elemental iron.

Also disclosed is a method of altering the composition of the gut bacterial microbiome in a subject, the method comprising administering to the subject a composition comprising (a) a microbe expressing ferritin and (b) elemental iron in an amount of at least 3% by weight on a dry matter basis of the microbe expressing ferritin and the elemental iron.

BRIEF DESCRIPTION OF THE DRAWINGS

FIG. 1A shows the amino acid sequence of human H-ferritin (SEQ ID NO: 1).

FIG. 1B shows the cDNA sequence of human H-ferritin (SEQ ID NO: 2). The start (ATG) and stop (TAA) codons are bolded, and the BamHI (at 5' end of sequence) and XhoI (at 3' end of sequence) restrictions sites are underlined.

FIG. 5 is the study calendar for the experiments utilized to test Composition A in Example 1.

FIG. 9 is the FACIT Fatigue Questionnaire that subjects completed daily or weekly over the time-course of Example 1. The Questionnaire was used under license from facit.org.

FIG. 11(A)-(F) is the SF-36 Questionnaire that subjects completed weekly over the time-course of Example 1.

FIG. 14 is the Gastrointestinal Symptoms Questionnaire that subjects completed daily/weekly (as the case may be) during screening (up to −4 weeks), daily for weeks 1−4 and then weekly for weeks 5-10 of Example 1.

DETAILED DESCRIPTION

Figure 2:
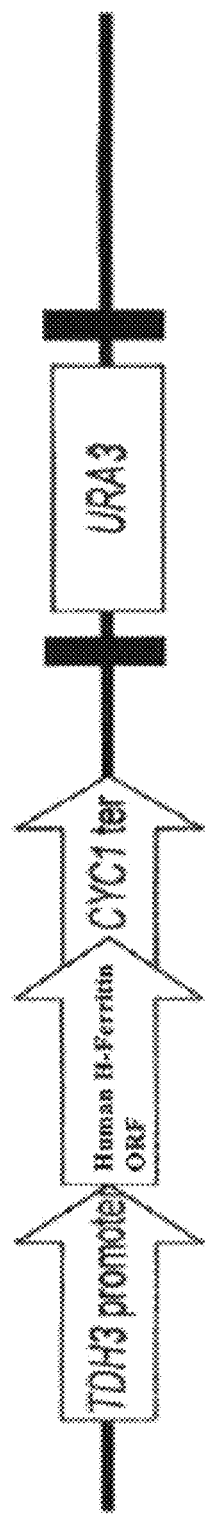
FIG. 2 shows the structure of a gene cassette for expressing H-ferritin under the control of the yeast TDH3 transcriptional promoter. H-ferritin ORF—open-reading frame encoding human H-ferritin; CYC1ter—transcriptional terminator from the yeast CYC1 gene; filled rectangles—loxP sites; URA3—selectable marker.

For purposes of the following detailed description, it is to be understood that the invention may assume various alternative variations and step sequences, except where expressly specified to the contrary. Moreover, other than in any operating examples, or where otherwise indicated, all numbers such as those expressing values, amounts, percentages, ranges, subranges and fractions may be read as if prefaced by the word "about," even if the term does not expressly appear. Accordingly, unless indicated to the contrary, the numerical parameters set forth in the following specification and attached claims are approximations that may vary depending upon the desired results to be obtained by the present invention. At the very least, and not as an attempt to limit the application of the doctrine of equivalents to the scope of the claims, each numerical parameter should at least be construed in light of the number of reported significant digits and by applying ordinary rounding techniques. Where a closed or open-ended numerical range is described herein, all numbers, values, amounts, percentages, subranges and fractions within or encompassed by the numerical range are to be considered as being specifically included in and belonging to the original disclosure of this application as if these numbers, values, amounts, percentages, subranges and fractions had been explicitly written out in their entirety.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

As used herein, unless indicated otherwise, a plural term can encompass its singular counterpart and vice versa, unless indicated otherwise. For example, although reference is made herein to "a" species of yeast, a combination (i.e., a plurality) of these components can be used. In addition, in this application, the use of "or" means "and/or" unless specifically stated otherwise, even though "and/or" may be explicitly used in certain instances.

As used herein, "including," "containing" and like terms are understood in the context of this application to be synonymous with "comprising" and are therefore open-ended and do not exclude the presence of additional undescribed and/or unrecited elements, materials, ingredients and/or method steps.

As used herein, "consisting of" is understood in the context of this application to exclude the presence of any unspecified element, ingredient and/or method step.

As used herein, "consisting essentially of" is understood in the context of this application to include the specified elements, materials, ingredients and/or method steps "and those that do not materially affect the basic and novel characteristic(s)" of what is being described.

As used herein, "patient" or "subject" means animals, including mammals, including humans, a canine, a feline, a bovine, an equine, a porcine, a primate, and/or a rodent.

As used herein, "pharmaceutical composition" means any chemical or biological composition, material, agent or the like that is capable of inducing a therapeutic effect when properly administered to a subject, including the composition, material, agent or the like in an inactive form and active metabolites thereof, where such active metabolites may be formed in vivo.

As used herein, an "iron deficiency disorder" includes a disorder or disease related to iron deficiency, iron uptake, and/or iron metabolism and includes disorders, diseases, or symptoms to which functional iron deficiency, iron deficiency, anemia, and iron deficient anemia are known to contribute; i.e., iron deficiency may take various forms. As used herein, "functional iron deficiency" refers to a condition in which subjects have a TSAT of 20%-50% and/or a serum ferritin concentration of 50 ng/mL to 700 ng/mL, but who exhibit symptoms of fatigue or other symptoms commonly associated with disorders or diseases related to iron deficiency, iron uptake, and/or iron metabolism based on responses to a health-related quality of life questionnaire. Such symptoms include dizziness, low blood pressure, rapid heart rate and heart palpitations, shortness of breath, paleness or yellowing of the skin, headaches, and the like. As used herein, "iron deficiency" refers to a condition in which subjects have a TSAT of <20% and a serum ferritin concentration of <50 ng/ml; subjects may exhibit symptoms commonly associated with disorders or diseases related to iron deficiency, iron uptake, and/or iron metabolism based on responses to a health-related quality of life questionnaire. Anemia refers to a condition in which subjects have a hemoglobin concentration of <13 g/dL; subjects may exhibit symptoms commonly associated with disorders or diseases related to iron deficiency, iron uptake, and/or iron metabolism based on responses to a health-related quality of life questionnaire. As used herein, "iron deficient anemia" refers to a condition in which subjects have a TSAT of <20%, a serum ferritin concentration of <50 ng/ml, and a hemoglobin concentration of <13 g/dL; subjects may exhibit symptoms commonly associated with disorders or diseases related to iron deficiency, iron uptake, and/or iron metabolism based on responses to a health-related quality of life questionnaire. Examples of iron deficiency disorders include iron deficiencies caused by insufficient dietary intake or absorption of iron. Iron deficiency disorders may be related to, for example, malnutrition, pregnancy (including the postpartum period), heavy uterine bleeding, chronic disease (including chronic kidney disease), cancer, renal dialysis, gastric bypass, multiple sclerosis, restless leg syndrome, diabetes (e.g. Type I and Type II diabetes), insulin resistance, and attention deficit disorders.

As used herein, a "gut microbiome disorder" refers to an imbalance of a patient or subject's microbiome. In particular, a gut microbiome disorder refers to elevated relative abundance of genus of bacteria that negatively impact the gut microbiome, such as, for example, *Klebsiella*, Enterobacteriales, Enterobacteriaceae, *Clostridium*, Anaerosporobacter, and/or Pygmaiobacter.

As used herein, "treat," "treatment," or "treating" means a therapeutic, prophylactic or preventative measure provided to a patient or subject with the intention of preventing the development or altering the pathology or symptoms experienced by the patient or subject, such as, e.g., those resulting from a disorder, which may include an iron deficiency disorder or a gut microbiome disorder. A "treatment" administered to a patient or subject may achieve any clinically or quantitatively measurable reduction in the condition for which the patient or subject is being treated up to and including complete elimination. Accordingly, "treatment" refers to both therapeutic treatment and prophylactic or preventative measures. "Treatment" may also be specified as palliative care. Those in need of treatment include those already with one or more iron-deficiency disorder as well as those in which the disorder is to be prevented.

As used herein, "dietary management" means treatment of a condition through administration of a medical food, a food ingredient, or a dietary supplement.

As used herein, "ingestible" means capable of being taken into the body orally.

As used herein, a "salt" refers to an ionic compound made up of metal cations and non-metallic anions and having an overall electrical charge of zero. Salts may be hydrated or anhydrous.

As used herein, "dry matter," with respect to a composition of the present invention, means that the composition has no more than 10% water by weight based on total weight of the composition.

As used herein, "dry matter basis" means a method of expressing the concentration of a component in a composition by expressing the component's concentration in terms of the dry matter content.

As used herein, an "adverse event" means any untoward medical occurrence in a subject consuming the composition of the present invention, and which does not necessarily have a causal relationship with such treatment.

As used herein, "transferrin saturation (TSAT)" means the ratio of serum iron to total iron-binding capacity (TIBC).

As used herein, "total iron-binding capacity" or "TIBC" means the total amount of iron that can be bound with serum proteins.

As used herein, "16S rRNA gene" means the portion of DNA conserved across all known bacterial species that contains variable regions that allow for bacterial identification within an environmental sample.

As used herein, "Alpha Diversity" means the measure that evaluates bacterial diversity within each environmental sample through the assessment of species richness, or the amount of unique bacterial species within a sample, and species evenness, or the abundance distribution of each bacterial specie, within a sample.

As used herein, "Beta Diversity" means the measure that evaluates bacterial diversity between environmental samples through the assessment of the phylogenetic distance between the bacterial communities of each environmental sample.

As used herein, "Bioinformatics" means a method of study that incorporates both computational science and biological techniques.

As used herein, "QIIME 2" refers to the data analysis package utilized for analyzing microbial abundance data within a terminal.

As used herein, "Species Richness" means the amount of unique species within a community.

As used herein, "Taxon" means a taxonomic group of any rank, such as a species, family, or class.

Disclosed herein, according to the present invention, is a composition comprising, or consisting essentially of, or consisting of, (a) a microbe expressing ferritin and (b) elemental iron in an amount of at least 3% by weight on a dry matter basis of the microbe expressing ferritin and the elemental iron.

Also disclosed herein, according to the present, is an ingestible comprising, or consisting essentially of, or consisting of, (a) a microbe expressing ferritin and (b) elemental iron in an amount of at least 3% by weight on a dry matter basis of the microbe expressing ferritin and the elemental iron. The ingestible may be a food, a medical food, a food ingredient, or combinations thereof.

Also disclosed, according to the present invention, is a dietary supplement comprising, or consisting essentially of, or consisting of, (a) a microbe expressing ferritin and (b) elemental iron in an amount of at least 3% by weight on a dry matter basis of the microbe expressing ferritin and the elemental iron.

Also disclosed is a pharmaceutical composition comprising, or consisting essentially of, or consisting of, (a) a microbe expressing ferritin and (b) elemental iron in an amount of at least 3% by weight on a dry matter basis of the microbe expressing ferritin and the elemental iron.

Also disclosed is a method for treating a subject comprising, or consisting essentially of, or consisting of, administering to the subject a composition comprising, or consisting essentially of, or consisting of, (a) a microbe expressing ferritin and (b) elemental iron in an amount of at least 3% by weight on a dry matter basis of the microbe expressing ferritin and the elemental iron the composition.

Also disclosed is a method of altering the composition of the gut bacterial microbiome in a subject, the method comprising, or consisting essentially of, or consisting of, administering to the subject a composition comprising, or consisting essentially of, or consisting of, (a) a microbe expressing ferritin and (b) elemental iron in an amount of at least 3% by weight based on dry weight of the microbe expressing ferritin and the elemental iron.

Any nutritional, non-pathogenic, or ingestible microbe may be used. As used herein, "non-pathogenic" means microbes that are unable to cause a disease. The microbe may be grown specifically for the purpose of iron supplementation or it may be the product of another process (e.g., fermentation).

Suitable examples of microbes useful in the present invention include, but are not limited to, a fungus, an alga, a bacterium, a protozoan, virus, microscopic helminths, microorganisms, or combinations thereof. For example, recombinant microbe strains suitable for nutritional supplementation of iron can store iron in a form having high bioavailability for mammals, including humans, such as those that meet the Generally Regarded As Safe (GRAS) requirements for human consumption. Other microbes that can be used in processes to produce therapeutic compounds also may be used in the composition of the present invention. The fungus may be, for example, a yeast. Non-limiting examples of yeast include various species of the genus *Saccharomyces*, such as *S. cerevisiae, S. sake, S. ellipsoidens*, and *S. pombe*, and various species of the genus *Pichia*. Other non-limiting examples of yeast include various species of the genus *Torulopsi*, such as *T. utilis*. Non-limiting examples of algae include various species of the genus *Chlamydomonas* and non-limiting examples of bacteria include various species of the genus *Lactococcus*. The microbe may contain impurities that may contribute to the weight of a composition of the present invention, but these weights are excluded from the total dry matter weight of the composition.

As mentioned above, the microbe expresses ferritin. Suitable ferritin comprises mammalian H-ferritin subunits. The H-ferritin subunits may be human H-ferritin (FTH1) (SEQ ID NO: 1; see FIG. 1A; see also FIG. 1B). The H-ferritin can also be a naturally-occurring or synthetic homologue or variant of human H-ferritin. The H-ferritin homologue may have 80% to 100% sequence identity to human H-ferritin, such as at least 80%, 81%, 82%, 83%, 84%, 85%, 86%, 87%, 88%, 89%, 90%, 91%, 92%, 93%, 94%, 95%, 96%, 97%, 98%, or 99% sequence identity with human H-ferritin and retains the ability to bind iron and form a multi-subunit ferritin-iron complex (described below), but can be mutated to provide varying binding and disassociation strengths between the iron and the ferritin. Optionally, the ferritin may further comprise L-ferritin. For example, the ferritin subunit may comprise at least 20% H-ferritin as compared to L-ferritin, such as about 20%, 30%, 40%, 50%, 60%, 70%, 80%, 90%, or 100% H-ferritin as compared to L-ferritin. Optionally, all of the ferritin subunits (i.e. 100% of the ferritin subunits) may be H-ferritin.

According to the present invention, the H-ferritin can be recombinant H-ferritin. For example, the H-ferritin can be human H-ferritin, or a homologue thereof, produced in a microbial strain comprising a polynucleotide sequence encoding the H-ferritin under the control of an appropriate promoter. Expression of ferritin may be extra-chromosomal (episomal) or may be chromosomally integrated.

For example, the microbe may be a strain of recombinant microbe expressing ferritin from a chromosomally integrated H-ferritin expression cassette. The H-ferritin coding sequence is placed under the control of an appropriate yeast promoter in an iron-storage expression cassette to produce high enough levels of the iron-storage protein for the yeast to serve as a suitable vehicle for iron supplementation. Suitable yeast promoters are known in the art and include promoters that induce a high level of constitutive expression and promoters whose expression can be regulated by environmental conditions. In addition, the genetic constitution of the yeast can be further manipulated to achieve a variety of potentially advantageous outcomes. For example, proteolysis may be manipulated to enhance the stability of the iron-storage protein or iron transport mechanisms, including but not limited to those of the cell surface, the vacuole, or the mitochondria, can be manipulated to achieve desirable outcomes such as altering the iron concentration in specific cellular compartments. In addition, the yeast may be altered in other manners to manipulate the level of iron in the iron-storage protein or cellular compartments. The iron content of the yeast may be regulated by adding known amounts of an iron compound to the medium in which the yeast are grown. Using the recombinant yeast, iron supplementation for humans and other animals can be accomplished by any of a number of means including, but not limited to, consumption or ingestion of yeast. The yeast may be grown specifically for the purpose of iron supplementation or they may be the by-product of another process (e.g., fermentation).

The composition of the present invention may optionally further comprise a second microbe. As used herein, the term "second" with respect to a microbe refers to a separate and distinct microbe and does not necessarily means that only two microbes are present. The second microbe may comprise any of the microbes discussed above. The second microbe may comprise a microbe that expresses ferritin, a microbe that does not express ferritin, or a combination thereof. The second microbe may additionally or alternatively comprise a probiotic.

The composition of the present invention may optionally further comprise a prebiotic that promotes the growth of beneficial bacteria in the gut microbiome.

The composition of the present invention also comprises elemental iron. The elemental iron may form a ferritin-iron complex with the ferritin described above. A source of the elemental iron may be an iron salt, an organic iron complex, an elemental iron nanoparticle, or combinations thereof. Examples of suitable iron salts include, but are not limited to, iron sulfate. As used herein, "iron containing complexes" or "iron complexes" are compounds which contain iron in the (II) or (III) oxidation state, complexed with an organic compound. Examples of suitable iron complexes include, but are not limited to, iron polymer complexes, iron carbohydrate complexes, and iron aminoglycosan complexes. These complexes are commercially available and/or can be synthesized by methods known in the art. Suitable non-limiting examples of iron carbohydrate complexes include iron saccharide complexes, iron oligosaccharide complexes, and iron polysaccharide complexes, such as iron carboxymaltose, iron sucrose, iron polyisomaltose (iron dextran), iron polymaltose (iron dextrin), iron gluconate, iron sorbital, and iron hydrogenated dextran, which may be further complexed with other compounds, such as sorbitol, citric acid and gluconic acid (for example iron dextrin-sorbitol-citric acid complex and iron sucrose-gluconic acid complex), and mixtures thereof. Suitable non-limiting examples of iron aminoglycosan complexes include iron chondroitin sulfate, iron dermatin sulfate, iron keratan sulfate, each of which may be further complexed with other compounds, and mixtures thereof. Examples of iron aminoglycosan complexes include but are not limited to iron hyaluronic acid, iron protein complexes, and mixtures thereof.

The elemental iron may be present in the composition in an amount of at least 3% by weight on a dry matter basis of the microbe expressing ferritin and the elemental iron, such as at least 5% by weight, such as at least 5.5% by weight, and may be present in an amount of no more than 15% by weight on a dry matter basis of the microbe expressing ferritin and the elemental iron, such as no more than 10% by weight, such as no more than 8% by weight. The elemental iron may be present in the composition in an amount of 3% by weight to 15% by weight on a dry matter basis of the microbe expressing ferritin and the elemental iron, such as 5% by weight to 10% weight, such as 5.5% by weight to 8% by weight.

The elemental iron may be present in the composition in an amount of at least 13 mg, such as at least 50 mg, at least 75 mg, and may be present in an amount of no more than 1000 mg, such as no more than 700 mg, such as no more than 300 mg. The elemental iron may be present in the composition in an amount of 13 mg to 1000 mg, 50 mg to 700 mg, such as 75 mg to 300 mg.

According to the present invention, at least 60% of the elemental iron may be complexed with the ferritin, such as at least 75% of the elemental iron, and 100% of the elemental iron may be complexed with the ferritin, such as no more than 90%. According to the present invention, 60% to 100% of the elemental iron may be complexed with the ferritin, such as 75% to 90%.

Any of the compositions described herein may be included in an ingestible item. In examples, the microbe may be included in the ingestible item. For example, the ingestible item may be a medical food, a food, a food ingredient, or combinations thereof. In other examples, any of the compositions described herein may be in the form of a suppository. In other examples, any of the compositions described herein may be a dietary or nutritional supplement. In other examples, any of the compositions described herein may be a pharmaceutical composition.

The compositions described herein may be in the form of a dry powder, a dispersion of the dry powder in a liquid, a suspension of the dry powder in a liquid, suppository, foam enema, liquid enema, or the like and may be formulated in such a manner as to be administered orally or rectally. The compositions of the present invention may include a pharmaceutically acceptable carrier or diluent (described herein) to form a solution, dispersion, emulsion, microemulsion, suspension, syrup, elixir or the like such that the materials may be swallowed or expectorated. pH adjusters (i.e., acids, or bases) may be included to adjust pH to the appropriate level, and/or antibacterial and antifungal agents may be included to prevent the action of microorganisms. Pharmaceutical compositions also may include formulations that control or slow release of the agent from the body. In some instances, the pharmaceutical composition may be included in a dispenser, such as a syringe, dosing vial, and the like.

Examples of ingestible diluents or carriers are sugars such as monosaccharides, disaccharides, and the like, excipients such as cocoa butter and waxes; oils such as peanut oil, cottonseed oil, safflower oils, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; other non-toxic compatible lubricants such as sodium lauryl sulfate and magnesium stearate; coloring agents, releasing agents, coating agents, preservatives and antioxidants according to the judgment of the formulator.

The compositions described herein may be expelled from a pressurized container, or may be in the form of powders, granules, or lozenges. Examples of suitable binders and fillers include, but are not limited to, magnesium stearate, microcrystalline cellulose, cellulose gel, cellulose gum, carboxymethyl cellulose, wood pulp, soy lecithin, glycine, monosodium glutamate, vegetable protein, seaweed or extract, carrageenan, or combinations thereof.

As used herein, the term "pharmaceutically acceptable" means acceptable for use in the pharmaceutical and veterinary arts, compatible with other ingredients of the formulation, and not toxic or otherwise unacceptable commensurate with a reasonable benefit/risk ratio. As used herein, "pharmaceutically acceptable carrier" includes any and all solvents, diluents, or other liquid vehicle, dispersion or suspension aids, surface active agents, isotonic agents, thickening and emulsifying agents, stabilizers, preservatives, solid binders, lubricants, and the like, as suited to the particular dosage form desired. Remington's Pharmaceutical Sciences Ed. By Gennaro, Mack Publishing, Easton, PA 1995 provides various carriers used in formulating pharmaceutical compositions and known techniques for the preparation thereof.

The skilled artisan understands that various factors influence the dosage required to treat a patient effectively, and that accordingly the dosage and administration may be chosen by the attending physician in view of the patient to be treated and may be adjusted for sufficient levels of the active agent(s) or to maintain the desired effect. Additional factors that may be taken into account include the severity of the disease state, e.g., intermediate or advanced stage of disease; age, weight, gender and overall health of the patient; diet, time and frequency of administration; form of iron deficiency; route of administration; drug combinations; reaction sensitivities; prior treatments; and tolerance/response to therapy. Pharmaceutical compositions may be administered, for example, every 30 minutes, hourly or daily; multiple times per day; weekly, multiple times per week; bi-weekly; monthly; and the like.

The active agents of the invention may be used to treat any of the diseases, disorders, or the like disclosed herein and may be administered as a therapeutically effective dose appropriate for the patient or subject to be treated. As described above, the therapeutic dose of the compositions of the present invention may be decided by the attending physician within the scope of sound medical judgment and experience. For the active agent, the therapeutically effective dose may be estimated initially in cell culture assays or in animal models such as mice, rats, rabbits, dogs, or pigs. Animal cell models may be used to achieve or determine a desirable concentration and total dosing range and route of administration, which may be used to determine a useful range of dosage and routes for administration in humans. Further, clinical studies and individual patient response may determine the recommended therapeutic dose.

A therapeutically effective dose of one of the compositions described herein may be administered at a dosage level of at least 13 mg of elemental iron per dose, such as at least 50 mg per dose, such as at least 75 mg per dose, and may be administered at a dosage level of no more than 1000 mg per dose, such as no more than 700 mg per dose, such as no more than 300 mg per dose. A therapeutically effective dose of one of the compositions described herein may be administered at a dosage level of 13 mg to 1000 mg of elemental iron per dose, such as 50 mg to 700 mg per dose, such as 75 mg to 300 mg per dose. As described herein, the dosage level may be administered as a single dose administered to the subject or patient, or through multiple administrations that achieve the dosage level over the course of a day. The dosage level may also be a total amount of iron administered for multiple times per week, weekly, bi-weekly, or monthly administration divided by the number of days between administration, wherein the dose administers iron in a dosage level described above on a per day average.

As described above, the methods described herein generally include the administration of any of the compositions described herein to a subject. The method may comprise, or consist essentially of, or consist of, administering a composition comprising, or consisting essentially of, or consisting of, (a) a microbe expressing ferritin and (b) elemental iron in an amount of at least 3% by weight on a dry matter basis of the microbe expressing ferritin and the elemental iron; wherein at least 60% of the elemental iron is complexed with the ferritin. For example, disclosed herein is a method for treating a subject comprising administering to the subject any of the compositions described herein. The administering may comprise administering to the subject a therapeutically effective amount of at least one of the compositions described herein. As used herein, the term "therapeutically effective amount" is an amount of the composition indicated for treatment (i.e., modulating or ameliorating symptoms or conditions of iron deficiency) while not exceeding an amount which may cause adverse effects. A therapeutically effective dose may increase or decrease over the course of treatment. Methods for evaluating the effectiveness or toxicity of therapeutic treatments are known to those of skill in the art, e.g., ED50 (the dose is therapeutically effective in 50% of the population) and LD50 (the dose is lethal to 50% of the population). The dose ratio of toxic to therapeutic effects is the therapeutic index, and it is expressed as the ratio, LD50/ED50. Notably, ED50 and LD50 may vary with age or condition of the subject.

The composition may be administered as a single dose or as multiple doses (i.e., first, second, third, etc. doses) administered contemporaneously or sequentially, such that administration of a first dose of the composition is followed by administration of a second dose of the composition, or vice versa. When the first and second doses are administered sequentially, the method may comprise waiting a period of time between the administration of the doses compositions. First, second, third, etc. doses may comprise the same or different amounts of elemental iron. As used herein, the term "sequentially" refers to a treatment protocol in which administration of a first dose of a composition of the present invention follows administration of a second dose of a composition of the present invention. As used herein, the term "contemporaneously" refers to administration of a first dose of a composition of the present invention and administration of a second dose of a composition of the present invention, wherein the first and second doses are separate and are administered at substantially the same time.

According to the present invention, the iron-deficiency of a subject may be treated by administering to the subject any of the compositions described herein, such as administering a therapeutically effective amount of any of the compositions described herein. For example, a method of treating a subject may comprise, or consist essentially of, or consist of, administering to the subject a composition comprising (a) a microbe expressing ferritin and (b) elemental iron in an amount of at least 3% by weight based on dry weight of the microbe expressing ferritin and the elemental iron. The administering may comprise oral administration or rectal administration. The subject may be determined to have at least one of the following prior to the administering: functional iron deficiency; iron deficiency; anemia; iron deficient anemia, or a gut microbiome disorder.

According to the present invention, the TSAT, serum ferritin, and/or hemoglobin concentration are measured and/or health assessments are made, such as by having a subject complete a health-related quality of life questionnaire. Examples of such questionnaires include the FACIT Fatigue Scale (available from FACIT Group) and the SF-36 Questionnaires (available from RAND Corporation). A recommendation of administering a composition of the present invention can be made based on the presence of the % TSAT, serum ferritin concentration, hemoglobin concentration, and/or scores based on responses to the health-related quality of life questionnaires, such as SF-36 Vitality Domain score, SF-36 Pain score, and/or FACIT Fatigue score. A composition of the present invention, such as a therapeutically effective amount, may be subsequently administered to treat the iron deficiency disorder.

According to the present invention, the composition of the gut bacterial microbiome in a subject may be altered by administering to the subject any of the compositions described herein. For example, a method of altering the composition of the gut bacterial microbiome in a subject may comprise, or consist essentially of, or consist of, administering to the subject a composition comprising (a) a microbe expressing ferritin and (b) elemental iron in an amount of at least 3% by weight based on dry weight of the microbe expressing ferritin and the elemental iron. The administering may comprise an oral or rectal administration. A composition of the present invention, such as a therapeutically effective amount, may be administered to treat a gut microbiome disorder.

The method of altering the composition of the gut bacterial microbiome in a subject may comprise modulating the relative abundance of Gammaproteobacteria class bacteria and/or Clostridia bacteria in a subject's gut. The Gammaproteobacteria class bacteria comprise bacteria from the Enterobacteriales order, Enterobacteriaceae family, and/or *Klebsiella* genus. The Clostridia class bacteria comprise bacteria from the *Clostridium*, Anaerosporobacter, and/or Pygmaiobacter genera. The relative abundance of Gammaproteobacteria class bacteria and/or Clostridia class bacteria may be reduced by at least −2 as determined by linear discriminant analysis, as described in the Examples below.

The method of altering the composition of the gut bacterial microbiome in a subject may comprise modulating the relative abundance of Erysipelotrichia class bacteria and/or Clostridia class bacteria in a subject's gut. The Erysipelotrichia class bacteria comprise bacteria from the Erysipelotrichales order, Erysipelotrichaceae family, *Candidatus* genus, and/or *Stoquefichus* species. The Clostridia class bacteria comprise bacteria from the Ruminococcaceae family. The relative abundance of Erysipelotrichia class bacteria and/or Clostridia class bacteria may be increased at least +2 as determined by linear discriminant analysis, as described in the Examples below.

The method of altering the composition of the gut bacterial microbiome in a subject may comprise reducing the biofilm formation in a subject's gut. The reduction in biofilm formation may be as determined by PICRUSt analysis, as described in the Examples below.

The method of altering the composition of the gut bacterial microbiome in a subject may comprise reducing the bacterial chemotaxis in a subject's gut. The reduction in bacterial chemotaxis may be as determined by PICRUSt analysis, as described in the Examples below Any of the methods of the present invention may comprise, or consist essentially of, or consist of the following:
  (a) identifying a subject suitable for or in need of treatment by a composition of the present invention by at least one of the following: (i) TSAT less than 20% and/or serum ferritin less than 50 ng/ml; (ii) hemoglobin less than 13 g/dL; and/or (iii) symptoms commonly associated with disorders or diseases related to iron deficiency, iron uptake, and/or iron metabolism based on responses to a health-related quality of life questionnaire;
  (b) administering to the patient a composition comprising, or consisting essentially of, or consisting of (i) a microbe expressing ferritin and (ii) elemental iron in an amount of at least 3% by weight on a dry matter basis of the microbe expressing ferritin and the elemental iron; and
  (c) assessing therapeutic effectiveness and/or tolerability of the composition.

Any of the methods of the present invention may comprise, or consist essentially of, or consist of the following:
  (a) identifying a subject suitable for or in need of treatment by a composition of the present invention by at least one of the following: (i) TSAT less than 20% and/or serum ferritin less than 50 ng/ml; (ii) hemoglobin less than 8 g/dL; and/or (iii) symptoms commonly associated with disorders or diseases related to iron deficiency, iron uptake, and/or iron metabolism based on responses to a health-related quality of life questionnaire;
  (b) administering to the subject a composition comprising, or consisting essentially of, or consisting of one of the compositions of the present invention at a dosage level of at least 13 mg of elemental iron per dose; and
  (c) assessing therapeutic effectiveness and/or tolerability of the composition.

The step of assessing therapeutic effectiveness and/or tolerability may comprise assessing any of the blood measurements described herein and/or assessing a subject's response to any of the qualitative questionnaires described herein.

Any of the methods of the present invention may further comprise dietary management. In examples, the subject being treated by the methods is not iron deficient. In examples, the subject being treated by the methods has an iron deficient disorder. The iron deficient disorder may be functional iron deficiency, iron deficiency, anemia, or iron deficient anemia.

The present invention is based on the surprising discovery that use of a microbe as the expression platform for ferritin/iron complexes for bioavailability to subjects repletes iron, improves the microbiome, improves quality of life, and avoids many of the severe gastrointestinal ("GI") side effects typically experienced by patients receiving conventional treatments such as $FeSO_4$. A patient or subject receiving treatment with the composition of the present invention according to the method of the present invention may experience quantitative improvements including an increase in hemoglobin concentration and a decrease in total iron binding capacity, as well as qualitative improvements to quality of life experienced by the patient or subject as demonstrated by increases to the FACIT Fatigue Questionnaire, SF-36 Bodily Pain Questionnaire, and SF-36 Vitality Questionnaire. Furthermore, it has been surprisingly discovered that the patient or subjects experience none or less of the gastrointestinal side effects associated with other iron supplements, such as iron sulfate, as reported by the patient or subject receiving the treatment. The inventors have surprisingly discovered that the lack of gastrointestinal side effects may be due to the surprisingly positive effect treatment with the composition of the present invention according to the methods of the present invention has on the patient or subject's microbiome. The inventors have demonstrated these surprising results by evaluating the patient or subject's microbiome both before, during and after treatment. It has been surprisingly discovered that treatment does not negatively impact the bacterial species richness of the patient or subject's microbiome while increasing the relative abundance of species of genus of bacteria that do not negatively impact the gut microbiome (e.g., *Candidatus*, Erysipelotrichales, Erysipelotrichia, Erysipelotrichaceae, and/or Ruminococcaceae) while reducing the relative abundance of species of genus of bacteria that do negatively impact the gut microbiome (e.g., *Klebsiella*, Enterobacteriales, Enterobacteriaceae, *Clostridium*, Anaerosporobacter, and/or Pygmaiobacter). Accordingly, treatment with the composition of the present invention according to the method of the present invention surprisingly improves the patient or subject's overall gut microbiome, in addition to improving quantitative and qualitative measures of the patient or subject's iron deficiency disorder. For example, according to the present invention, at least 1 week, such as at least 2 weeks, such as at least 4 weeks, such as at least 6 weeks, such as at least 8 weeks, such as at least 10 weeks, such as at least 12 weeks, following the administering of any of the compositions described herein:
  (a) the average observed bacterial species richness in the subject's gut is substantially the same as the average observed bacterial species richness in the subject's gut prior to the administering, wherein "substantially the same" with respect to bacterial species richness means a change of less than 20% relative to baseline average observed bacterial species;
  (b) the relative abundance of *Klebsiella*, Enterobacteriales, Enterobacteriaceae, *Clostridium*, Anaerosporobacter, and/or Pygmaiobacter in the subject's gut is at least −2 as determined by linear discriminant analysis;
(c) the relative abundance of *Candidatus*, Erysipelotrichales, Erysipelotrichia, Erysipelotrichaceae, and/or Ruminococcaceae in the subject's gut is at least +2 as determined by linear discriminant analysis;
(d) the level of biofilm formation (cpm) in the subject's gut as determined by PICRUSt analysis is reduced by at least 1% relative to levels prior to the administering, such as reduced by at least 2%, such as reduced by at least 3%, such as reduced by at least 4%;
(e) the level of biofilm formation (cpm) in the subject's gut as determined by PICRUSt analysis is reduced by at least 50 cpm compared to levels prior to the administering, such as reduced by at least 100 cpm, such as reduced by at least 300 cpm, such as reduced by at least 400 cpm;
(f) the predicted bacterial chemotaxis in the subject's gut as determined by PICRUSt analysis is reduced by at least 1% relative to predicted levels prior to the administering, such as reduced by at least 5%, such as reduced by 10%, such as reduced by 20%;
(g) the predicted bacterial chemotaxis in the subject's gut as determined by PICRUSt analysis is reduced by at least 200 cpm compared to the predicted cpm prior to the administering, such as reduced by at least 300 cpm, such as reduced by at least 500 cpm, such as reduced by at least 700 cpm;
(h) the subject's hemoglobin concentration is increased by at least 1% relative to the hemoglobin concentration prior to the administering, such as increased by at least 2.5%, such as increased by at least 5%, such as increased by at least 7.5%;
(i) the subject's hemoglobin concentration is increased by at least 0.1 g/dL relative to the hemoglobin concentration prior to the administering, such as increased by at least 0.3 g/dL, such as increased by at least 0.5 g/dL, such as increased by at least 1.0 g/dL;
(j) the subject's total iron binding capacity is decreased by at least 2.5% relative to the total iron binding capacity prior to the administering, such as decreased by at least 5%, such as decreased by at least 7.5%, such as decreased by at least 10%;
(k) the subject's total iron binding capacity is decreased by at least 40 µg/dL relative to the total iron binding capacity prior to the administering, such as decreased by at least 60 µg/dL;
(l) the subject's FACIT Fatigue Score is increased by at least 3 points relative to the FACIT Fatigue Score prior to the administering;
(m) the subject's SF-36 Bodily Pain Score is increased by at least 5 points relative to the SF-36 Bodily Pain Score prior to the administering;
(n) the subject's SF-36 Vitality Score is increased by at least 5 points relative to the SF-36 Vitality Score prior to the administering; and/or
(o) the mean incidence of the subject's gastrointestinal symptoms per week are less than a two-fold increase compared to the mean incidence of the subject's gastrointestinal symptoms per week prior to the administering as a determined by a qualitative ranking scale.

Without being bound by theory, it is posited that iron complexed with ferritin is sequestered and actively transported across the intestine by yet to be identified ferritin receptors, avoiding many of the side effects of conventional iron supplements, which deliver iron in the $Fe^{+2}$ state, known to be poorly absorbed, more toxic, and to promote rapid expansion of iron scavenging bacteria (siderophores) in the gut, leading to GI distress.

Other aspects and advantages of the present invention will be understood upon consideration of the following illustrative examples. The examples are not to be construed in any way as limiting the scope of this invention. Those of skill in the art should, in light of the present disclosure, appreciate that changes can be made in the specific embodiments which are disclosed and still obtain a like or similar result without departing from the spirit and scope of the invention.

ASPECTS

Aspect 1. A composition comprising (a) a microbe expressing ferritin and (b) elemental iron.

Aspect 2. The composition of Aspect 1, wherein elemental iron is present in an amount of at least 3% by weight on a dry matter basis of the microbe expressing ferritin and the elemental iron.

Aspect 3. The composition of Aspects 1 or 2, wherein at least 60% of the elemental iron is complexed with the ferritin.

Aspect 4. The composition of any of the preceding Aspects, wherein the ferritin comprises mammalian H-ferritin or a homologue thereof.

Aspect 5. The composition of Aspect 4, wherein the mammalian H-ferritin is human H-ferritin or a homologue thereof.

Aspect 6. The composition of Aspects 4 or 5, wherein the homologue has at least 80% sequence identity with human H-ferritin.

Aspect 7. The composition of any of the preceding Aspects, wherein a source of the elemental iron is an iron salt, an organic iron complex, an elemental iron nanoparticle, or combinations thereof.

Aspect 8. The composition of any of the preceding Aspects, wherein the microbe comprises a fungus, an alga, a virus, a microscopic helminth, a microorganism, a bacterium, a protozoan, or combinations thereof.

Aspect 9. The composition of any of the preceding Aspects, further comprising an amount of at least one filler.

Aspect 10. The composition of any of the preceding Aspects 1-8, wherein the composition consists essentially of (a) the microbe expressing ferritin and (b) the elemental iron.

Aspect 11. An ingestible item comprising the composition of any of the preceding Aspects.

Aspect 12. The ingestible item of Aspect 11, wherein the ingestible item is in the form of a medical food, a food, a food ingredient, or combinations thereof.

Aspect 13. A dietary supplement comprising the composition of any of the preceding Aspects 1-10.

Aspect 14. A pharmaceutical composition comprising the composition of any of the preceding Aspects 1-10.

Aspect 15. A method for treating a subject comprising administering to the subject a composition comprising the composition of any of the preceding Aspects 1-10.

Aspect 16. The method of Aspect 15, wherein the composition administered to the subject comprises at least 13 mg of elemental iron.

Aspect 17. The method Aspects 15 or 16, wherein the administering comprises a single dose.

Aspect 18. The method of any of Aspects 15-17, wherein the administering comprises more than one dose administered sequentially.

Aspect 19. The method of any of Aspects 15-18, wherein at least 1 week following the administering:

(a) the average observed bacterial species richness in the subject's gut is substantially the same as the average observed bacterial species richness in the subject's gut prior to the administering.

Aspect 20. The method of any of Aspects 15-19, wherein at least 1 week following the administering:
(b) the relative abundance of *Klebsiella*, Enterobacteriales, Enterobacteriaceae, *Clostridium*, Anaerosporobacter, and/or Pygmaiobacter in the subject's gut is at least −2 as determined by linear discriminant analysis.

Aspect 21. The method of any of Aspects 15-20, wherein at least 1 week following the administering:
(c) the relative abundance of *Candidatus*, Erysipelotrichales, Erysipelotrichia, Erysipelotrichaceae, and/or Ruminococcaceae in the subject's gut is at least +2 as determined by linear discriminant analysis.

Aspect 22. The method of any of Aspects 15-21, wherein at least 1 week following the administering:
(d) the level of biofilm formation in the subject's gut is reduced by at least 1% as determined by PICRUSt analysis relative to levels prior to the administering.

Aspect 23. The method of any of Aspects 15-22, wherein at least 1 week following the administering:
(e) the level of biofilm formation in the subject's gut as determined by PICRUSt analysis is reduced by at least 50 cpm compared to levels prior to the administering.

Aspect 24. The method of any of Aspects 15-23, wherein at least 1 week following the administering:
(f) the predicted bacterial chemotaxis in the subject's gut as determined by PICRUSt analysis is reduced by at least 1% relative to levels prior to the administering.

Aspect 25. The method of any of Aspects 15-24, wherein at least 1 week following the administering:
(g) the predicted bacterial chemotaxis in the subject's gut as determined by PICRUSt analysis is reduced by at least 200 cpm compared to the predicted cpm prior to the administering.

Aspect 26. The method of any of Aspects 15-25, wherein at least 1 week following the administering:
(h) the subject's hemoglobin concentration is increased by at least 1% relative to the hemoglobin concentration prior to the administering.

Aspect 27. The method of any of Aspects 15-26, wherein at least 1 week following the administering:
(i) the subject's hemoglobin concentration is increased by at least 0.1 g/dL relative to the hemoglobin concentration prior to the administering.

Aspect 28. The method of any of Aspects 15-27, wherein at least 1 week following the administering:
(j) the subject's total iron binding capacity is decreased by at least 2.5% relative to the total iron binding capacity prior to the administering.

Aspect 29. The method of any of Aspects 15-28, wherein at least 1 week following the administering:
(k) the subject's total iron binding capacity is decreased by at least 40 μg/dL relative to the total iron binding capacity prior to the administering.

Aspect 30. The method of any of Aspects 15-29, wherein at least 1 week following the administering:
(l) the subject's FACIT Fatigue Score is increase by at least 3 points relative to the FACIT Fatigue Score prior to the administering.

Aspect 31. The method of any of Aspects 15-30, wherein at least 1 week following the administering:
(m) the subject's SF-36 Bodily Pain Score is increased by at least 5 points relative to the SF-36 Bodily Pain Score prior to the administering.

Aspect 32. The method of any of Aspects 15-31, wherein at least 1 week following the administering:
(n) the subject's SF-36 Vitality Score is increased by at least 5 points relative to the SF-36 Vitality Score prior to the administering.

Aspect 33. The method of any of Aspects 15-32, wherein at least 1 week following the administering:
(o) the mean incidence of the subject's gastrointestinal symptoms per week are less than a two-fold increase relative to the mean incidence of the subject's gastrointestinal symptoms per week prior to the administering.

Aspect 34. The method of any of Aspects 15 or 17-33, wherein the administering comprises an average of at least 13 mg of elemental iron per day.

Aspect 35. The method of any of Aspects 15-34, wherein the treating comprises dietary management.

Aspect 36. The method of Aspect 35, wherein the subject is not iron deficient.

Aspect 37. The method of Aspect 35, wherein the subject has an iron deficiency disorder.

Aspect 38. A method of altering the composition of the gut bacterial microbiome in a subject, the method comprising administering to the subject a composition comprising the composition of any of Aspects 1-10.

Aspect 39. The method of any of Aspect 38, wherein at least 1 week following the administering:
(a) the average observed bacterial species richness in the subject's gut is substantially the same as the average observed bacterial species richness in the subject's gut prior to the administering.

Aspect 40. The method of Aspect 38 or 39, wherein at least 1 week following the administering:
(b) the relative abundance of *Klebsiella*, Enterobacteriales, Enterobacteriaceae, *Clostridium*, Anaerosporobacter, and/or Pygmaiobacter in the subject's gut is at least −2 as determined by linear discriminant analysis.

Aspect 41. The method of any of Aspects 38 to 40, wherein at least 1 week following the administering:
(c) the relative abundance of *Candidatus*, Erysipelotrichales, Erysipelotrichia, Erysipelotrichaceae, and/or Ruminococcaceae in the subject's gut is at least +2 as determined by linear discriminant analysis.

Aspect 42. The method of any of Aspects 38 to 41, wherein at least 1 week following the administering:
(d) the level of biofilm formation in the subject's gut is reduced as determined by PICRUSt analysis is reduced by at least 1% relative to levels prior to the administering.

Aspect 43. The method of any of Aspects 38 to 42, wherein at least 1 week following the administering:
(e) the level of biofilm formation in the subject's gut as determined by PICRUSt analysis is reduced by at least 50 cpm compared to levels prior to the administering.

Aspect 44. The method of any of Aspects 38 to 43, wherein at least 1 week following the administering:
(f) the predicted bacterial chemotaxis in the subject's gut as determined by PICRUSt analysis is reduced by at least 1% relative to levels prior to the administering.

Aspect 45. The method of any of Aspects 38 to 44, wherein at least 1 week following the administering:
(g) the predicted bacterial chemotaxis in the subject's gut as determined by PICRUSt analysis is reduced by at least 200 cpm compared to the predicted cpm prior to the administering.

Aspect 46. The method of any of Aspects 38 to 45, wherein at least 1 week following the administering:
(h) the subject's hemoglobin concentration is increased by at least 1% relative to the hemoglobin concentration prior to the administering.

Aspect 47. The method of any of Aspects 38 to 46, wherein at least 1 week following the administering:
(i) the subject's hemoglobin concentration is increased by at least 0.1 g/dL relative to the hemoglobin concentration prior to the administering.

Aspect 48. The method of any of Aspects 38 to 47, wherein at least 1 week following the administering:
(j) the subject's total iron binding capacity is decreased by at least 2.5% relative to the total iron binding capacity prior to the administering.

Aspect 49. The method of any of Aspects 38 to 48, wherein at least 1 week following the administering:
(k) the subject's total iron binding capacity is decreased by at least 40 µg/dL relative to the total iron binding capacity prior to the administering.

Aspect 50. The method of any of Aspects 38 to 49, wherein at least 1 week following the administering:
(l) the subject's FACIT Fatigue Score is increased by at least 3 points relative to the FACIT Fatigue Score prior to the administering.

Aspect 51. The method of any of Aspects 38 to 50, wherein at least 1 week following the administering:
(m) the subject's SF-36 Bodily Pain Score is increased by at least 5 points relative to the SF-36 Bodily Pain Score prior to the administering.

Aspect 52. The method of any of Aspects 38 to 51, wherein at least 1 week following the administering:
(n) the subject's SF-36 Vitality Score is increased by at least 5 points relative to the SF-36 Vitality Score prior to the administering.

Aspect 53. The method of any of Aspects 38 to 52, wherein at least 1 week following the administering:
(o) the mean incidence of the subjects gastrointestinal symptoms per week are less than a two-fold increase relative to the mean incidence of the subject's gastrointestinal symptoms per week prior to the administering.

Aspect 54. The method of any of Aspects 38 to 53, wherein the administering comprises an average of at least 13 mg of elemental iron per day.

Aspect 55. The method of any of Aspects 38 to 54, wherein the method of altering comprises dietary management.

EXAMPLES

Figure 3:
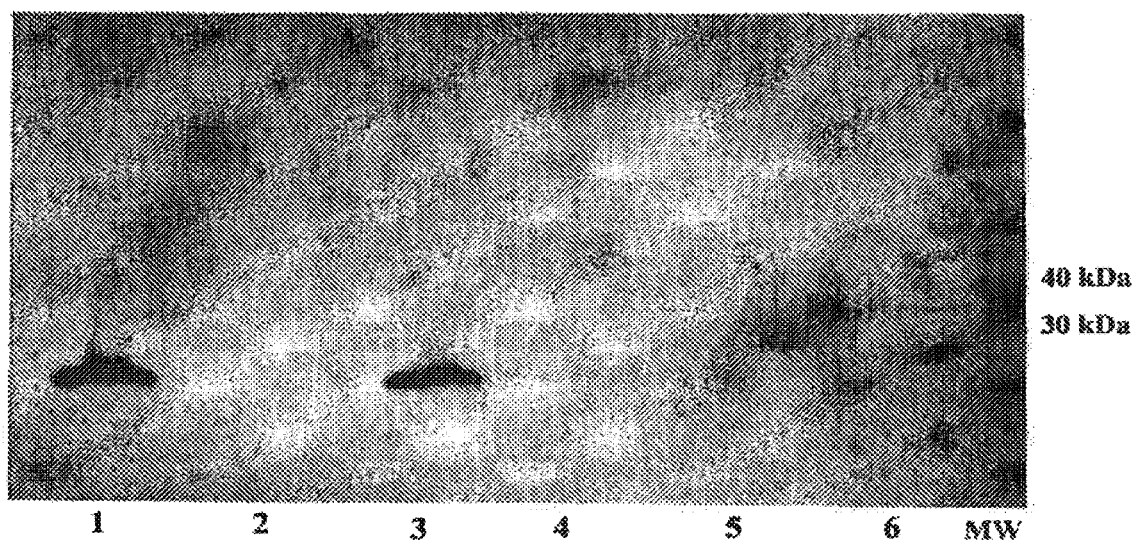
FIG. 3 shows a western blot demonstrating the effect of the chromosomal site of integration on the expression of recombinant H-ferritin in transformed yeast. Lane 1—H-ferritin in RLK3190; Lanes 2 and 4—H-ferritin in yeast strains having other chromosomal integration sites of the H-ferritin gene; Lane 3—H-ferritin in RLK3177, which contains a multicopy, extrachromosomal plasmid; Lane 5—no sample; Lane 6—purified His-tagged rH-ferritin; Lane 7—molecular weight markers.

Construction of Recombinant Yeast:

In each of Examples 1 and 2, an H-ferritin expression cassette for *S. cerevisiae*, shown in FIG. 2, expressing human H-ferritin under the control of the yeast constitutive TDH3 transcriptional promoter was generated by PCR from plasmid RLK/pL5659, which was derived from pAG426GPD-ccdB (AddGene, Cambridge, Mass.), by inserting the H-ferritin coding sequence and the URA3 gene. The PCR product was transformed into the yeast strain BY4741 and allowed to integrate into the yeast chromosome using standard methods, for example, as described in Hinnen et al., *PNAS USA* 75: 1929-1933, 1978. Yeast transformants containing the expression cassette were recovered via selectable marker, and lysates of transformed yeast were prepared in 50 mM Tris-HCl (pH 7.4), 150 mM NaCl using glass beads. Twenty-five µg of total protein, determined by the DC Protein Assay (Bio-Rad), were fractionated by SDS-PAGE and to transferred to a nitrocellulose filter. The blot was probed with H-ferritin polyclonal antibody diluted 1:2000 (Covance PA 1192). The secondary antibody was anti-rabbit IgG diluted 1:5000 (GE Amersham) and signal was detected using Western Lightning-ECL (Perkin Elmer). The results, shown in FIG. 3, indicate that the amount of expression of recombinant H-ferritin depends on the site of chromosomal integration. Recombinant strain RLK3190, containing a chromosomally integrated H-ferritin expression cassette, unexpectedly expressed dramatically higher levels of human H-ferritin compared with other chromosomal sites of integration. This level matches or exceeds the amount of H-ferritin produced by strain RLK3177, which contains an extrachromosomal plasmid bearing multiple copies of the H-ferritin expression cassette. In RLK3190, the expression cassette integrated at the chromosomal location of TDH3 by homologous recombination based on the homology between the TDH3 promoter on the expression cassette and the chromosomal gene. This cassette and others can readily be engineered for insertion at this site using standard techniques in the art.

The expression cassette in the RLK3190 strain constitutively produces human H-ferritin at high levels when it is integrated into the TDH3 locus on the yeast chromosome. Yeast transformants were grown in an iron-rich medium (6 mM FeSo4).

In Example 1, the composition was formed into a powder that contained 5.7% elemental iron by weight on a dry matter basis. The powder was encapsulated into 375 mg capsules for consumption (Composition A).

In Example 2, the composition was formed into a powder that contained 7.4% elemental iron by weight on a dry matter basis. The powder was encapsulated into 375 mg capsules for consumption (Composition B).

Example 1

Figure 4:
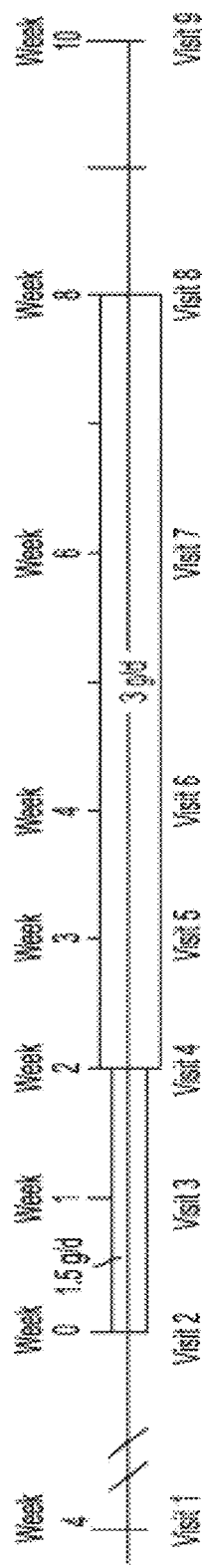
FIG. 4 is a schematic outlining the experimental protocol utilized to test Composition A in EXAMPLE 1.

The experimental protocol is illustrated in FIG. 4. The study calendar is shown in FIG. 5. Subjects were pre-screened and only non-anemic patients (hemoglobin ≥8 g/dL) were selected to participate in the study. All subjects were instructed to stop taking iron supplements and/or multivitamins containing iron (if any) for four weeks prior to initiation of the study.

Thirty-four subjects (demographics reported in Table 1) with iron deficiency (transferrin saturation (TSAT)<20% and serum ferritin <50 ng/mL) were instructed to take 1.5 g of Composition A/day, provided as four 375 mg capsules, for two weeks. Capsules were ingested directly with water. The content of iron in Composition A was about 57 mg of iron/gram of Composition A, making the initial intake level 85.5 mg of iron per day, which is about 50% of the standard of care daily recommendation for iron salts such as ferrous sulfate (165-195 mg per day) for subject with iron deficiency.

TABLE 1

| STUDY DEMOGRAPHICS | |
|---|---|
| Characteristics | (total number of subjects = 34) |
| Age, yrs | |
| Mean (SD) | 46 (14.4) |
| Min, max | 23, 76 |

TABLE 1-continued

STUDY DEMOGRAPHICS

| Characteristics | (total number of subjects = 34) |
|---|---|
| Sex, n (%) | |
| Men | 3 (9.0) |
| Women | 31 (91.0) |
| Race, n (%) | |
| Caucasian | 32 (94.0) |
| African American | 1 (3.0) |
| Asian | 1 (3.0) |
| American Indian or Alaska Native | 0 (0.0) |
| Native Haitian or Other Pacific Islander | 0 (0.0) |
| Other | 0 (0.0) |
| Ethnicity, n (%) | |
| Hispanic | 0 (0.0) |
| Not Hispanic | 34 (100.0) |
| Weight lb | |
| Mean (SD) | 198.6 (49.1) |
| Min, max | 125, 315 |

Tolerability of Composition A was monitored by direct questioning and recording adverse events and by completion of a weekly gastrointestinal discomfort questionnaire. Tolerability of Composition A also meant that a subject did not experience a dose limiting toxicity (GI discomfort described by the subject as intolerable or an adverse event classified as severe and related to Composition A).

All subjects tolerated 1.5 g/d of Composition A. The dose of Composition A then was increased to 3 g Composition A/day provided as eight 375 capsules, for six weeks. Capsules were ingested directly with water. As discussed above, the content of iron in Composition A was about 57 mg of iron/gram of Composition A, making the intake level 171 mg of iron per day, which is consistent with the standard of care daily recommendation for iron salts such as ferrous sulfate (165-195 mg per day) for subject with iron deficiency.

Blood Samples and Analysis

Blood samples (10 mL) were drawn at screening (Week −1), baseline (Week 0), and weekly thereafter (Weeks 1-10) and were analyzed to measure levels of hemoglobin, total iron binding capacity (TBIC), and transferrin saturation (TSAT). Data are reported in FIGS. 6-8 and are presented as the mean values for all subjects at each time point measured.

Figure 6:
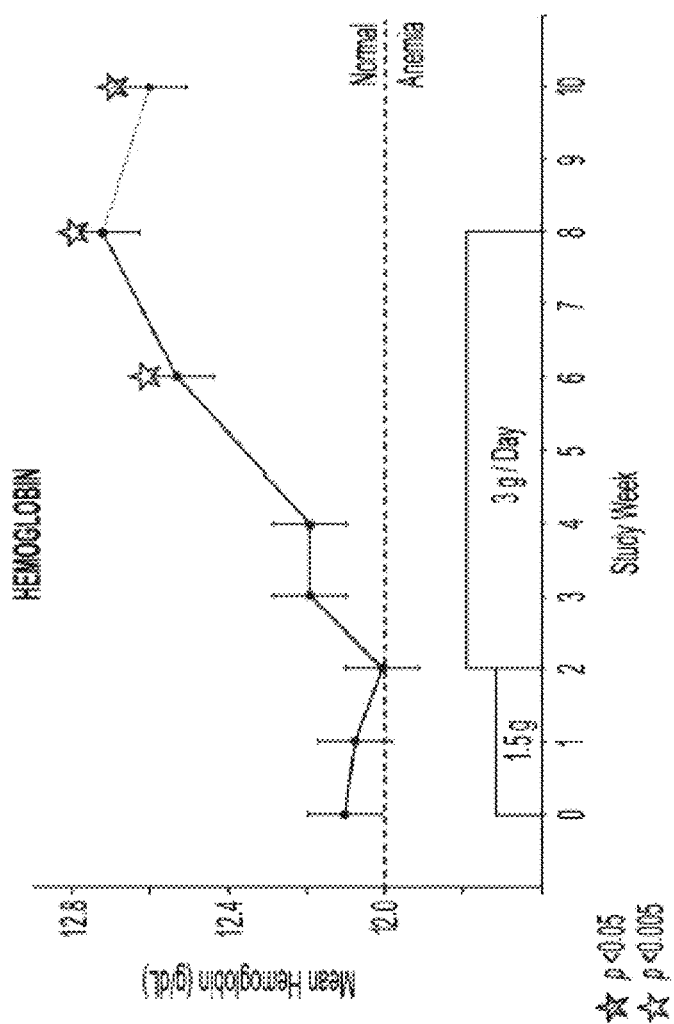
FIG. 6 is a graph reporting mean hemoglobin (g/dL) measured in subjects who were provided and consumed Composition A in Example 1.

As illustrated in FIG. 6, mean hemoglobin levels did not change significantly post-treatment with 1.5 g/d Composition A (Week 2) compared to baseline levels (Week 0). However, mean hemoglobin levels increased significantly between Week 2 (initiation of 3 g/d Composition A) and Week 8 (completion of treatment). At Week 10 (2 weeks following discontinuation of treatment), mean hemoglobin levels remained significantly elevated. While not wishing to be bound by theory, it is hypothesized that these data may be the result of a lag in hemoglobin synthesis following increased iron levels, rather than a non-responsiveness to the lower dose level utilized at the beginning of the experimental period.

Figure 7:
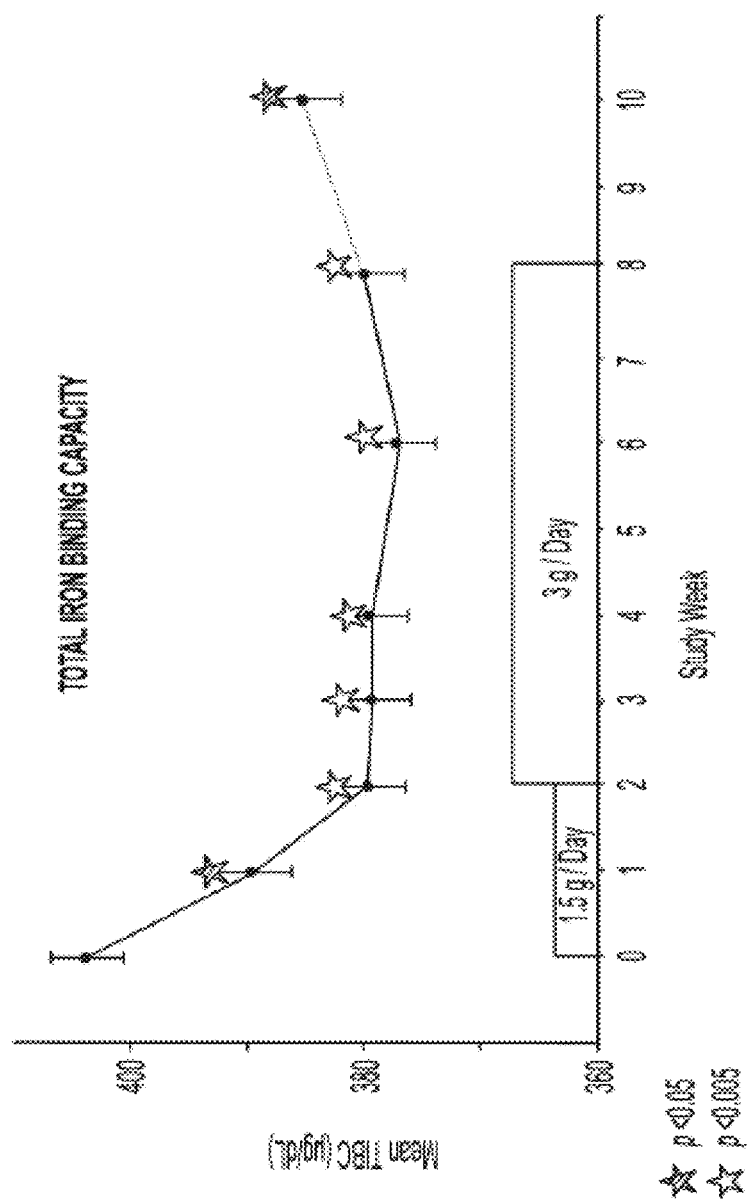
FIG. 7 is a graph reporting mean total iron binding capacity (TIBC; µg/dL) measured in subjects who were provided and consumed Composition A in Example 1.

As illustrated in FIG. 7, TIBC decreased significantly post-treatment with 1.5 g/d Composition A (Week 2) compared to baseline levels (Week 0) and decreased significantly between Week 2 (initiation of 3 g/d Composition A) and Week 8 (completion of treatment). At Week 10, TIBC remained significantly decreased.

Figure 8:
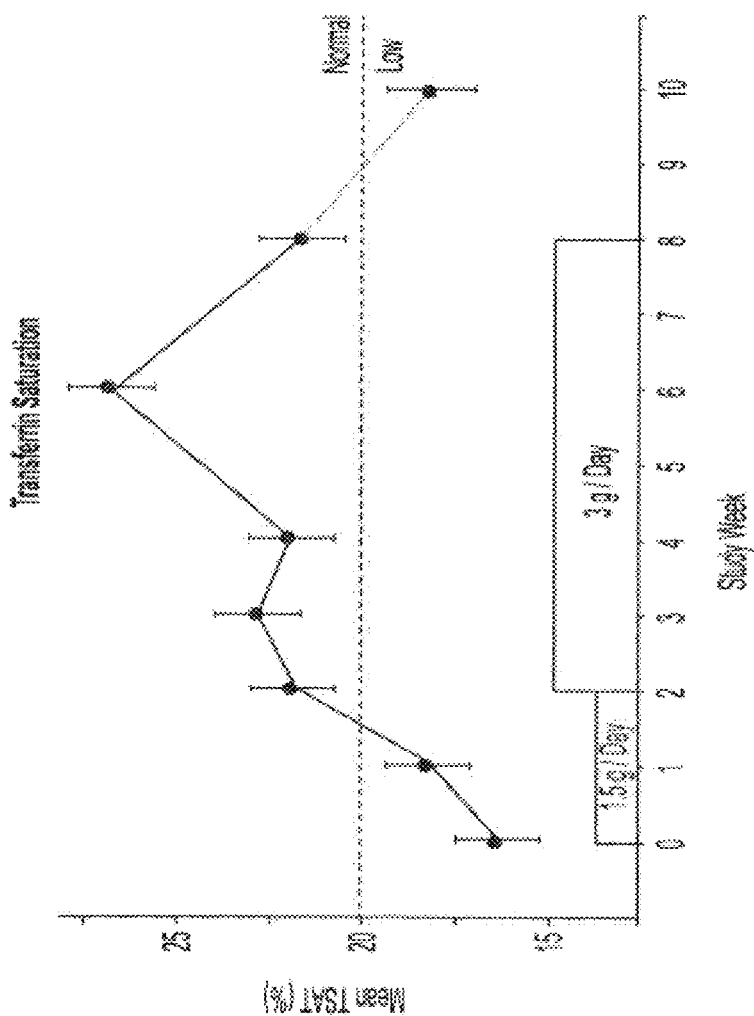
FIG. 8 is a graph reporting transferrin saturation (%) (calculated as serum iron/TIBC) in subjects who were provided and consumed Composition A in Example 1.

As illustrated in FIG. 8, the % transferrin saturation increased post-treatment with 1.5 g/d Composition A (Week 2) compared to baseline levels (Week 0) and reached a maximum at Week 6. The % transferrin saturation remained elevated at Week 8, but decreased at Week 10 to levels similar to baseline.

Health Surveys

Subjects were provided with a record book containing health survey questions. Subjects completed Functional Assessment of Chronic Illness Therapy (FACIT) Fatigue Questionnaire (FIG. 9) at screening (Week −1), baseline (Week 0), and weekly thereafter (Weeks 1-10). The FACIT Fatigue Questionnaire is a 13-item questionnaire that assesses self-reported fatigue and its impact upon daily activities and function. The 13-item Functional Assessment of Chronic Illness Therapy-Fatigue Scale (FACIT-F Scale) Scale uses a 5-point Likert-type scale (0=Not at all; 1=A little bit; 2=Somewhat; 3=Quite a bit; and 4=Very Much). The recall period for each question was "during the past 7 days". As each of the 13 items of the FACIT-F Scale ranges from 0-4, the range of possible scores was 0-52, with 0 being the worst possible score and 52 the best. To obtain the 0-52 score each negatively-worded item response was recoded so that 0 was a bad response and 4 was good response. For example, questions 1-6 and 9-13 had their scores inverted such that a response of 0 was recorded as a score of 4. All responses were added with equal weight to obtain the total score. In cases where some answers were missing, a total score was prorated from the score of the answered items, so long as more than 50% of the items (i.e., at least 7 of 13) were answered.

Figure 10:
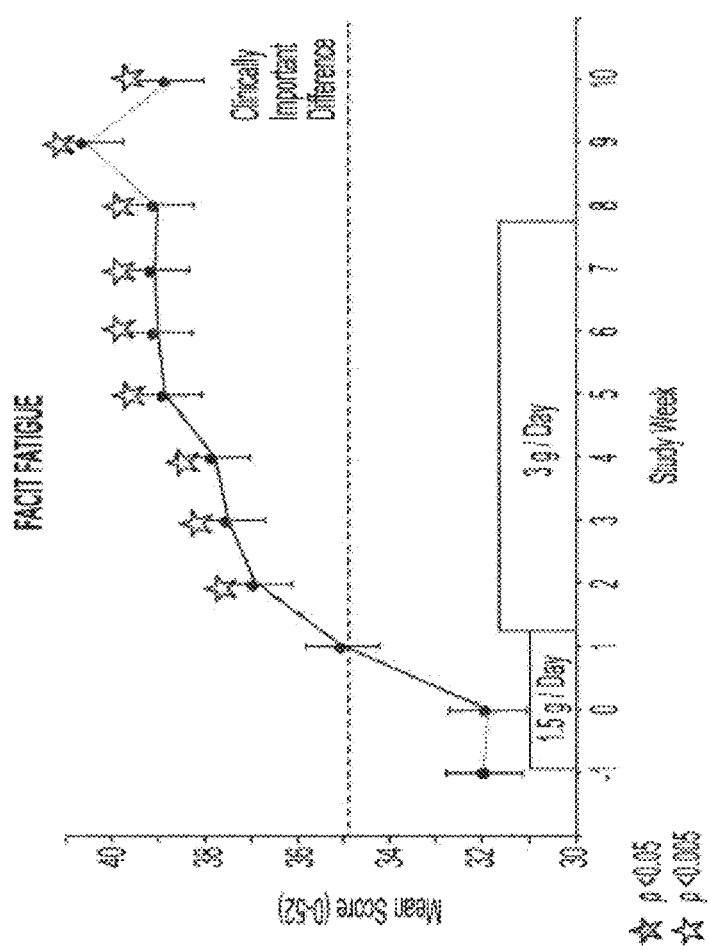
FIG. 10 is a graph reporting the mean FACIT Fatigue score in subjects who were provided and consumed Composition A in Example 1.

Data are reported in FIG. 10. FIG. 10 includes a dashed line identifying the score associated with what constitutes a Clinically Important Difference for the FACIT-F Scale as reported in J Pain Symptom Man 2002, 24(6):547-61. As used herein, the term "Clinically Important Difference" refers to the smallest change in a treatment outcome that an individual patient would identify as important and which would mandate a change in the patient's management. As shown in FIG. 10, a Clinically Important Difference was an increase in the FACIT score of at least 3 points following at least 1 week of treatment with Composition A compared to the score at baseline (Week −1; Week 0).

Subjects also completed the SF-36 Health Survey (FIG. 11) at screening (Week −1), baseline (Week 0), and weekly thereafter (Weeks 1-10). The SF-36 Health Survey is a set of generic, coherent, and easily administered quality-of-life measures prepared by RAND Corporation. These measures relied upon patient self-reporting. These questions addressed eight health domains: physical functioning, bodily pain, role limitations due to physical health problems, role limitations due to personal or emotional problems, emotional well-being, social functioning, energy/fatigue, and general health perceptions. The Survey also included a single item that provided an indication of perceived change in health.

Scoring the SF-36 Health Survey was a two-step process. First, precoded numeric values were recoded per the scoring key given in Table 2. All items were scored so that a high score defined a more favorable health state. In addition, each item was scored on a 0 to 100 range so that the lowest and highest possible scores were 0 and 100, respectively. Scores reported herein represent the percentage of total possible score achieved.

Second, items in the same scale were averaged together to create the 8 scale scores for each health domain. Table 3 lists the items averaged together to create each scale. Items that were left blank (missing data) were not taken into account when calculating the scale scores. Hence, scale scores reported herein represent the average for all items in the scale that the respondents answered.

TABLE 2

RECODING ITEMS

| Item numbers | Change original response category | To recoded value of: |
|---|---|---|
| 1, 2, 20, 22, 34, 36 | 1 → | 100 |
| | 2 → | 75 |
| | 3 → | 50 |
| | 4 → | 25 |
| | 5 → | 0 |
| 3, 4, 5, 6, 7, 8, 9, 10, 11, 12 | 1 → | 0 |
| | 2 → | 50 |
| | 3 → | 100 |
| 13, 14, 15, 16, 17, 18, 19 | 1 → | 0 |
| | 2 → | 100 |
| 21, 23, 26, 27, 30 | 1 → | 100 |
| | 2 → | 80 |
| | 3 → | 60 |
| | 4 → | 40 |
| | 5 → | 20 |
| | 6 → | 0 |
| 24, 25, 28, 29, 31 | 1 → | 0 |
| | 2 → | 20 |
| | 3 → | 40 |
| | 4 → | 60 |
| | 5 → | 80 |
| | 6 → | 100 |
| 32, 33, 35 | 1 → | 0 |
| | 2 → | 25 |
| | 3 → | 50 |
| | 4 → | 75 |
| | 5 → | 100 |

TABLE 3

AVERAGING ITEMS TO FORM SCALES

| Scale | Number of items | After recoding per Table 1, average the following items |
|---|---|---|
| Physical functioning | 10 | 3 4 5 6 7 8 9 10 11 12 |
| Role limitations due to physical health | 4 | 13 14 15 16 |
| Role limitations due to emotional problems | 3 | 17 18 19 |
| Energy/fatigue | 4 | 23 27 29 31 |
| Emotional well-being | 5 | 24 25 26 28 30 |
| Social functioning | 2 | 20 32 |
| Pain | 2 | 21 22 |
| General health | 5 | 1 33 34 35 36 |

Figure 12:
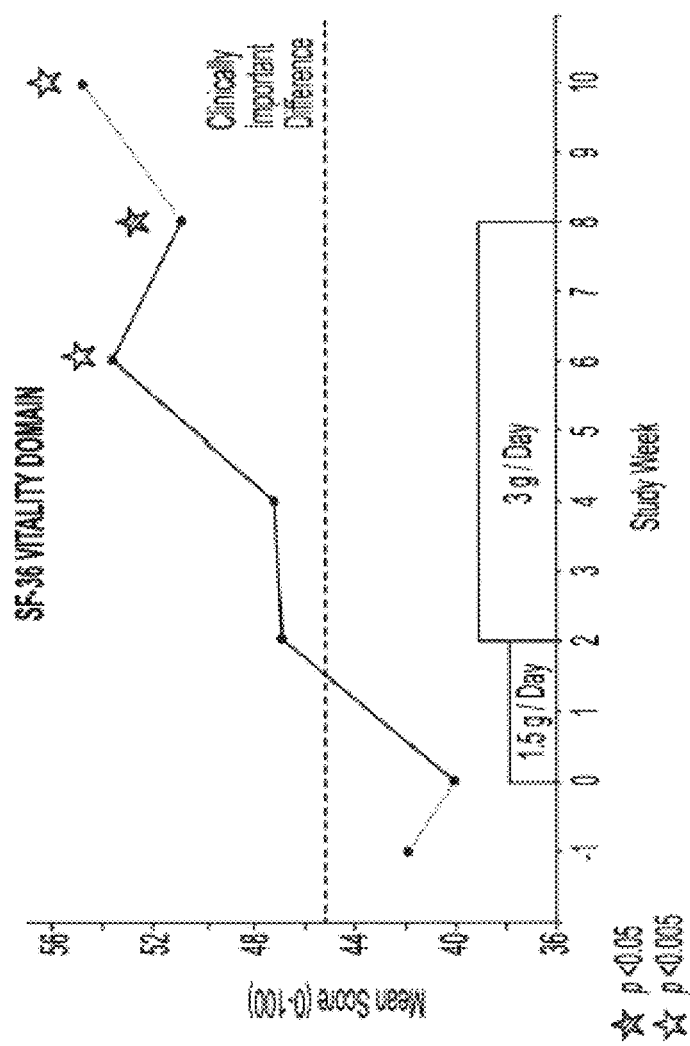
FIG. 12 is a graph reporting the mean SF-36 Vitality Domain score in subjects who were provided and consumed Composition A in Example 1.

Mean SF-36 Vitality Domain Scores are reported in FIG. 12. FIG. 12 includes a dashed line identifying the score associated with what constitutes a Clinically Important Difference for the vitality score of the SF-36 Health Survey as reported in J Pain Symptom Man 2002, 24(6):547-61. As shown in FIG. 12, the mean SF-36 Vitality Domain Score increased more than 5 points at Week 2 compared to baseline (Week 0) and remained elevated following treatment with 3 g/d Composition A at Week 8 (completion of treatment) and at Week 10.

Figure 13:
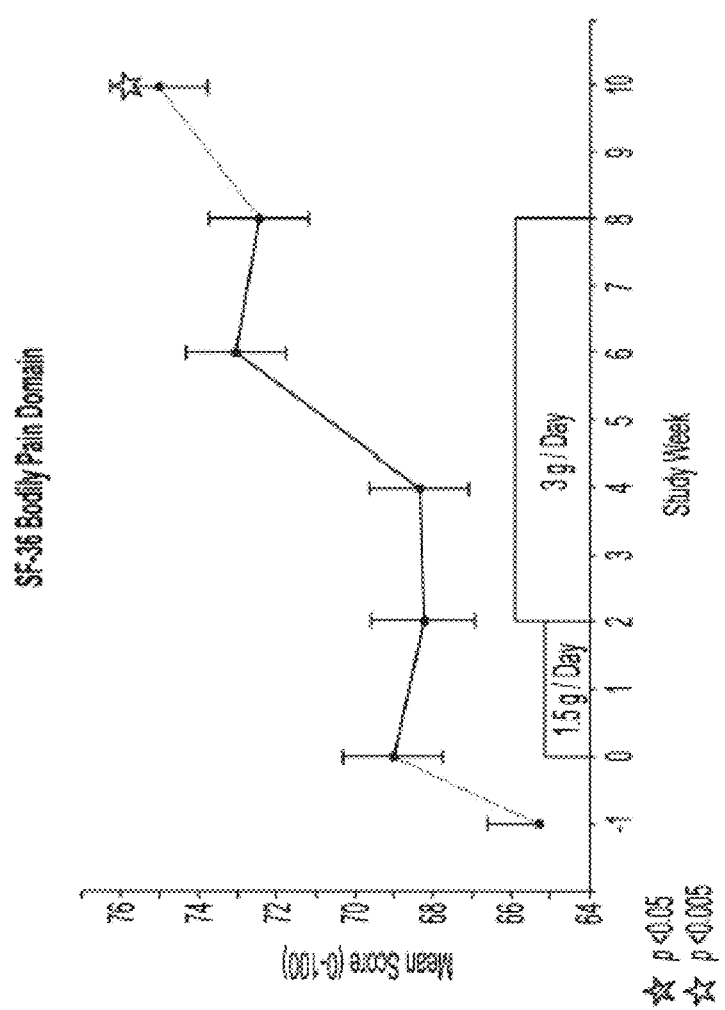
FIG. 13 is a graph reporting the mean SF-36 pain score in subjects who were provided and consumed Composition A in Example 1.

Pain Scores are reported in FIG. 13. As shown in FIG. 13, the mean SF-36 Pain Score increased at Week 6 and remained elevated at Week 8 (completion of treatment) and was significantly increased at Week 10 (post-treatment).

Figure 15:
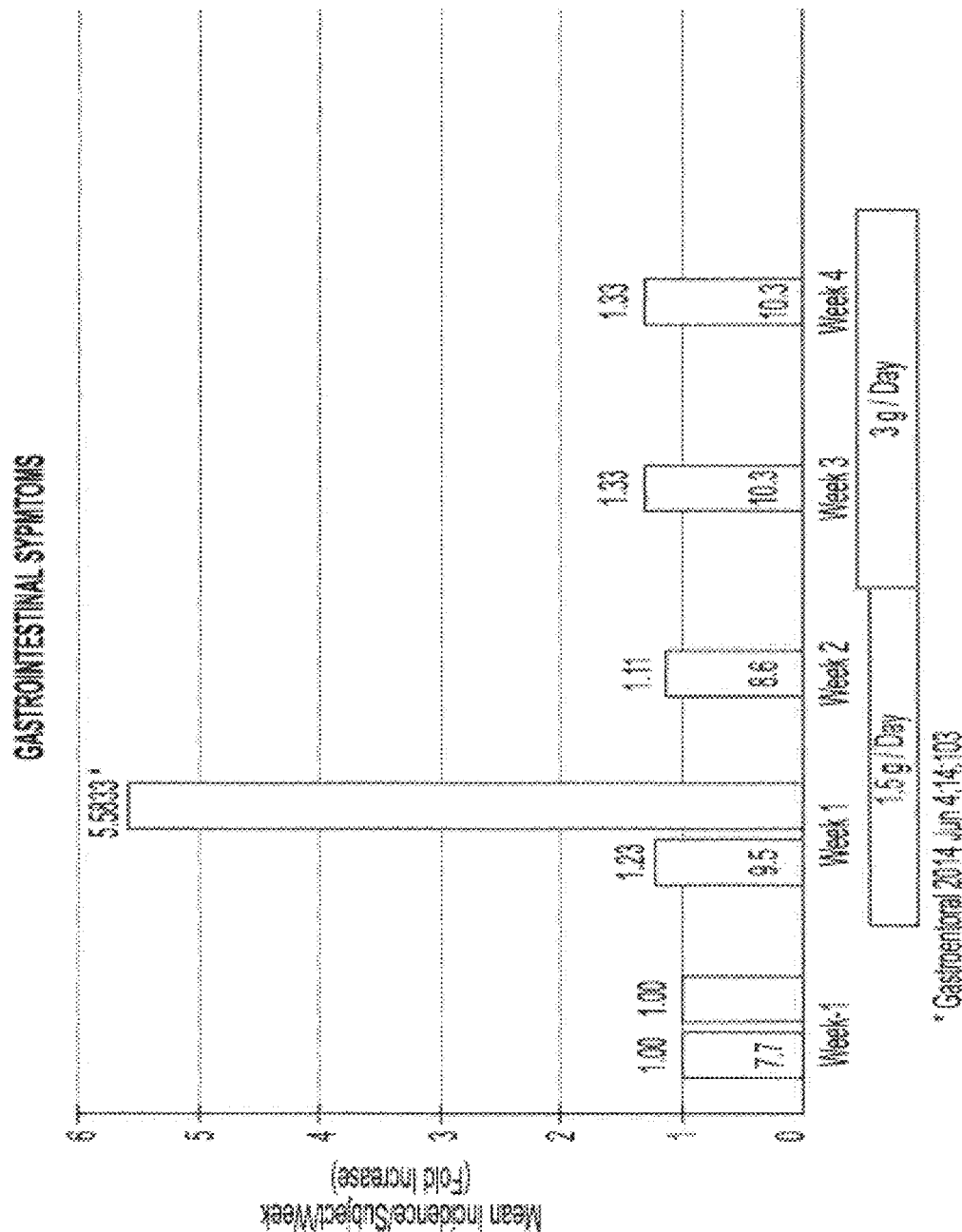
FIG. 15 is a graph reporting gastrointestinal symptoms in subjects who were provided and consumed Composition A in Example 1. Reported values are the mean of any reported symptom as a ratio of post-dosing:pre-dosing. At week 1, the bar indicating 5.5833 incidences per subject per week are from data reported in *Gastroenteral.* 2014 Jun. 4:14:103 in subjects treated with $FeSO_4$.

Subjects also completed a gastrointestinal symptom questionnaire (FIG. 14). This questionnaire is based on the questionnaire utilized in Nutrition & Metabolism 2013, 10:18. Data are reported in FIGS. 15 and 16. As shown in FIG. 15, symptom reports per subject per week went from 7.7 to 9-10, generating a ratio of post-dosing:pre-dosing of 1.1:1.3, compared to industry reports in which treatment with $FeSO_4$ resulted in symptom reports per subject per week of 6.7 vs. 1.2 symptom reports per subject per week for subjects receiving placebo (i.e., a 5.8× ratio) (see Nutrition & Metabolism 2013, 10:18). These data demonstrate that subjects who received Composition A had fewer symptom reports per subject per week than has been reported in the literature for patients treated with $FeSO_4$. Thus, treatment with Composition A is more tolerable to the gastrointestinal system than is treatment with the conventional $FeSO_4$.

Figure 16:
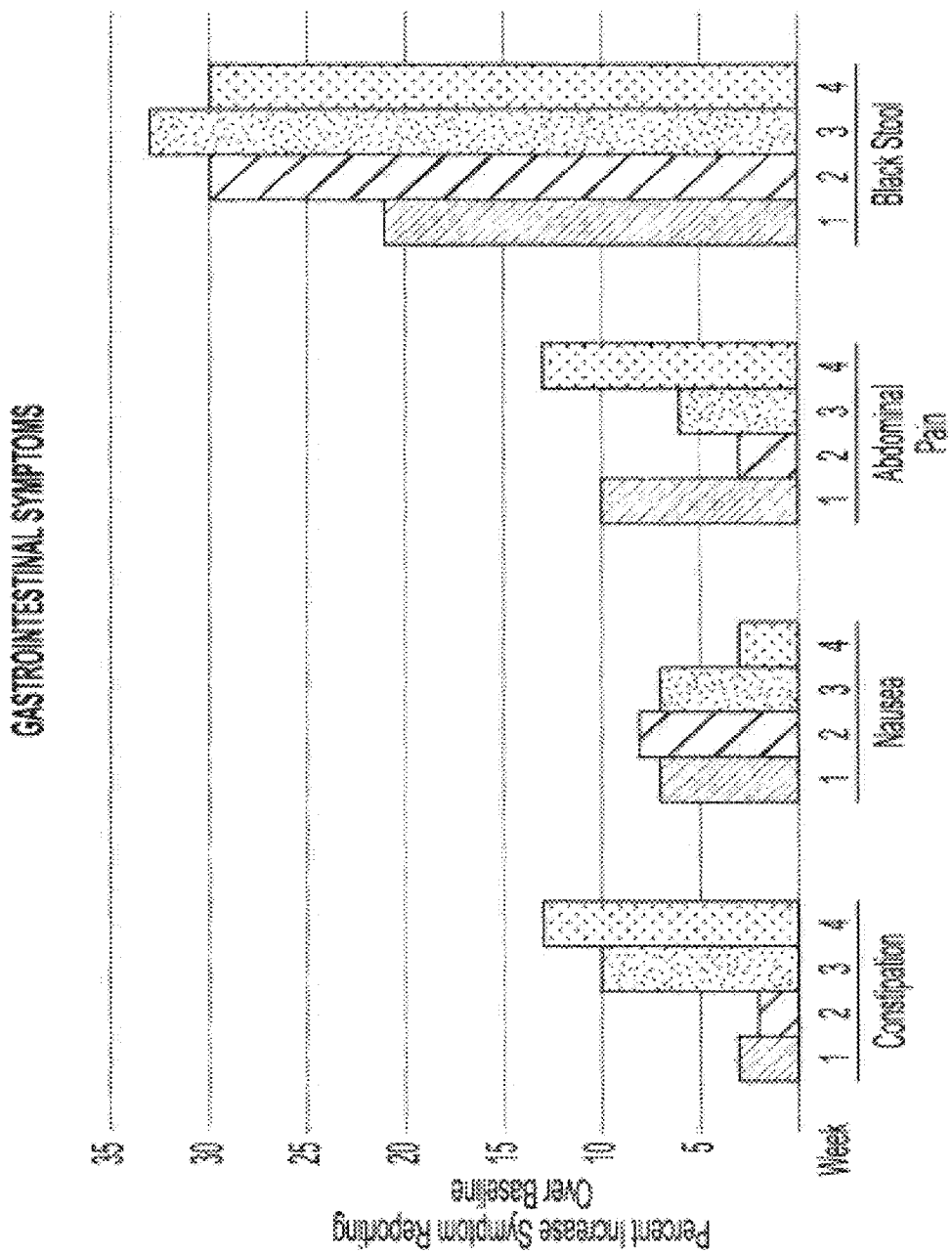
FIG. 16 is a graph reporting subjects reporting gastrointestinal symptoms (% increase over screening, Week −1) in Example 1 at Weeks 1 to 4.

FIG. 16 reports the % increase in gastrointestinal symptoms experienced by subjects treated with Composition A in Example 1 during Weeks 1-4. Although subjects experienced some gastrointestinal symptoms, the symptoms experienced during the 4 weeks did not worsen significantly with continued administration of Composition A.

Microbiome Samples and Analysis

Subjects were provided with home stool sample collection kits and instructed to return samples by mail to the stool analysis service provider (Wright Labs, LLC). As discussed in more detail below, DNA from stool were extracted and assessed for the phylogenetic makeup of the gut microbiome using illumina metagenomic sequencing. Analysis of select samples were further evaluated for species level DNA sequences in order to identify and quantify specific microbial flora and fauna of the gut. Data are reported as the mean values for all subjects at each time point measured.

DNA Extraction and Quantification:

Nucleic acid extractions were performed on approximately 0.25 g of each sample (or roughly 500 µL for liquid samples) using a Qiagen DNeasy Powersoil DNA Isolation kit following the manufacturer's instructions (Qiagen, Frederick, MD). The lysing step was performed using the Disruptor Genie cell disruptor (Scientific Industries). Finally, the genomic DNA was eluted in 50 µl of 10 mM Tris. Subsequent quantification was performed using a Qubit 2.0 Fluorometer (Life Technologies, Carlsbad, CA) with the double stranded DNA high sensitivity assay.

PCR Amplification:

Illumina iTag Polymerase Chain Reactions (PCR) were performed based on the Earth Microbiome Project's 16S rRNA amplification protocol (Walte J G, Fuhrman J A, Apprill A, Knight R. 2015. Improved Bacterial 16S rRNA Gene (V4 and V4-5) and Funrs W, Hyde E R, Berg-Lyons D, Ackermann G, Humphrey G, Parada A, Gilbert J A, Jansson J K, Caporasogal Internal Transcribed Spacer Marker Gene Primers for Microbial Community Surveys. mSystems 1). The volume of each reaction was 25 µL and contained (final concentrations) 1×PCR buffer, 0.8 mM dNTP's, 0.625 U Ex Taq DNA Polymerase (Takara), 0.2 µM 515F barcoded forward primer, 0.2 µM 806R reverse primer and ~10 ng of template DNA per reaction. PCR was carried out on a T100 Thermal Cycler (Bio-Rad, Hercules, CA) using the following cycling conditions: 98° C. for 3 min; then 35 cycles of 98° C. for 1 min, 55° C. for 40 s, and 72° C. for 1 min; final extension was at 72° C. for 10 min; then held at 4° C. PCR products were visualized on a 2% agarose E-Gel with ethidium bromide (Thermo Fisher Scientific) for bands at ~400 bp.

Library Purification, Verification and Sequencing:

PCR products were then combined (pooled) in an approximate equimolar manner. The pooled PCR products were then run on a 2% agarose gel with Gel Star Nucleic Acid Gel Stain (Lonza) for visualization. Bands of expected product length were cut from the gel using sterile scalpels and were subsequently purified using the QIAquick Gel Purification Kit (Qiagen, Frederick, MD). The pure library was then quantified using the Qubit 2.0 Fluorometer double stranded DNA high sensitivity assay (Life Technologies, Carlsbad, CA). Finally, each library on the sequencing run was combined (multiplexed) into one sequencing library by normalizing each library's input based on the number of samples per project to ensure even sequencing and coverage.

Prior to submission for sequencing, libraries were quality checked using a 2100 Bioanalyzer high sensitivity DNA analysis kit (Agilent Technologies, Santa Clara, CA). The sequencing library was stored at −20° C. until it was shipped on dry ice to Laragen Inc (Culver City, CA) for sequencing.

Library pools were size verified using the Fragment Analyzer on the ABI3730 and were quantified with a KAPA Library quantification kit (Kapa Biosystem, Wilmington, MA, USA). After dilution with EBT (Illumina) to a final concentration of 2 nM containing 15% PhiX V3 library control (Illumina, San Diego, CA, USA), the library pools were denatured for 5 min in an equal volume of 0.2M NaOH, then further diluted to 8 pM in HTI buffer (Illumina) and were sequenced using an Illumina MiSeq V2 500 cycle kit cassette with 16S rRNA library sequencing primers set for 250 basepair, paired-end reads. Overall sequencing run performance is evaluated by determining whether the sequencing run meets the Illumina specifications for quality scores and data output. Actual run performance varied based on sample type, quality, and clusters passing filter. Specifications are based on the Illumina PhiX control library at supported cluster densities.

Quality Filtering and De-Noising:

Demultiplexed paired end sequences were first imported within the QIIME 2 software (www.qiime2.org). Raw sequences were then subject to DADA2 merging, de-noising, filtration, and chimera removal (Callahan B J, McMurdie P J, Rosen M J, Han A W, Johnson A J A, Holmes S P, 2016. DADA2: High-resolution sample inference from Illumina amplicon data. Nat Methods). The following filtering parameters within DADA2 were utilized: forward reads were trimmed at base 248 and reverse reads were trimmed at base 229 prior to merging. The maximum expected error allowed was 0.5. For taxonomy identification, QIIME2 uses a classification method to assign taxa based on a Naive Bayes classifier and alignment tool to map data against the SIILVA database (Release 132).

Bioinformatics

Alpha Diversity Comparisons: Alpha diversity box plots were generated within the QIIME2 sequence analysis package using an unrarified taxonomy table. Samples with less than 7,000 sequences per sample were excluded from alpha diversity analyses. Multiple rarefactions were conducted on sequences across all samples to a maximum depth of 7,000 sequences, with a step size of 700, and 20 iterations at each step. Alpha diversities were then collated and plotted and compared using a two-sample 1-test and non-parametric Monte Carlo permutations (n=999).

Beta Diversity Comparisons: Principal coordinates analyses (PCoA) plots and PERMANOVA tests for significance were generated from a weighted UniFrac distance matrix made within QIIME2 from a CSS normalized OTU table (Paulson J N, Stine O C, Bravo H C, Pop M. 2013. Robust methods for differential abundance analysis in marker gene surveys. Nat Methods 10:1200-1202).

Figure 17:
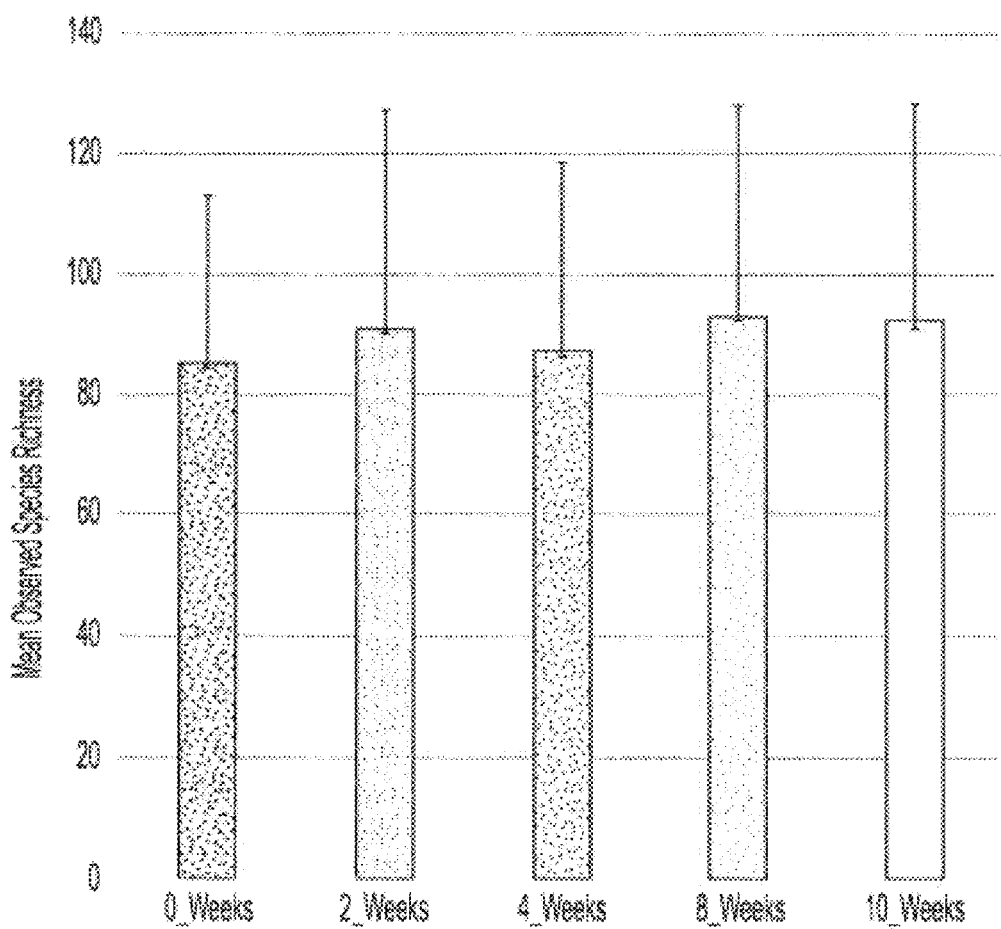
FIG. 17 is a graph showing the average observed species richness in gut bacterial microbiome of subjects who were provided and consumed Composition A in Example 1.

Average observed species richness is shown in FIG. 17. As illustrated, the average observed bacterial species richness in the subject's gut was substantially the same following at least 2 weeks of treatment with Composition A as the average observed bacterial species richness in the subject's gut prior to the administering.

Taxonomic LEfSe Enrichment Plots: Relative abundances of bacterial taxa were multiplied by 1 million and formatted as described in Segata et al. (Segata N, Izard J, Waldron L, Gevers D, Miropolsky L, Garrett W S, Huttenhower C. 2011. Metagenomic biomarker discovery and explanation. Genome Biol 12). Comparisons were made with "Timepoint" as the main categorical variable ("Class"). Alpha levels of 0.05 was used for the Kruskal-Wallis and 0.10 for the Wilcoxon test. Linear Discriminant Analysis (LDA) scores greater than 2.0 are displayed.

Figure 18:
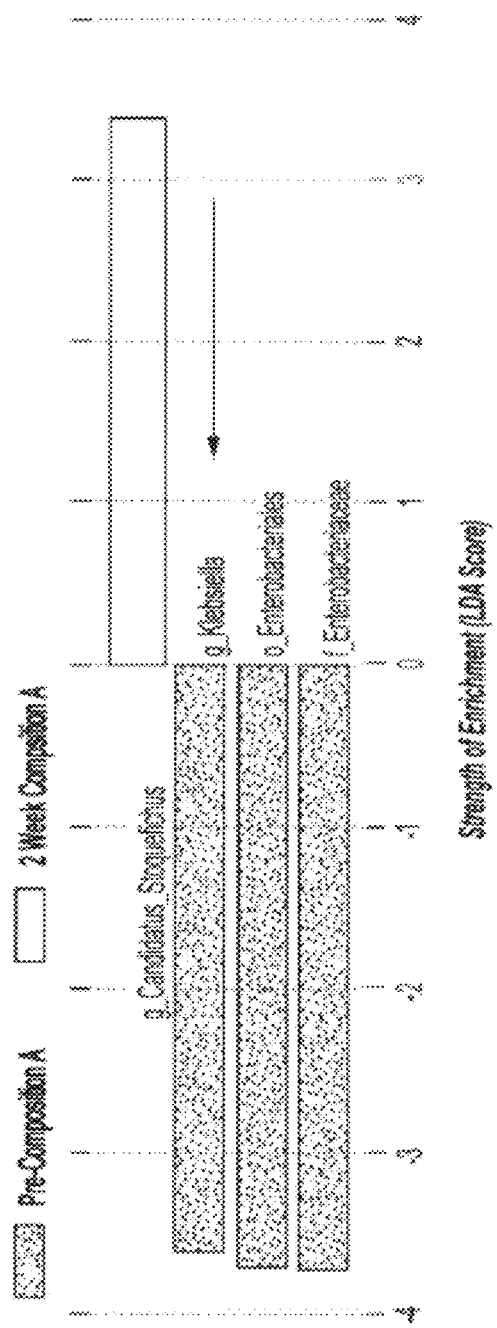
FIG. 18 is a graph showing the Strength of Enrichment (LDA Score) of observed species in the gut bacterial microbiome of subjects who were provided and consumed Composition A for 2 weeks in Example 1.

As shown in FIG. 18, the relative abundance of Klebsiella, Enterobacteriales, Enterobacteriaceae, Clostridium, Anaerosporobacter, and/or Pygmaiobacter in the subject's gut was at least −2 as determined by linear discriminant analysis following at least 2 weeks of treatment with Composition A.

Figure 19:
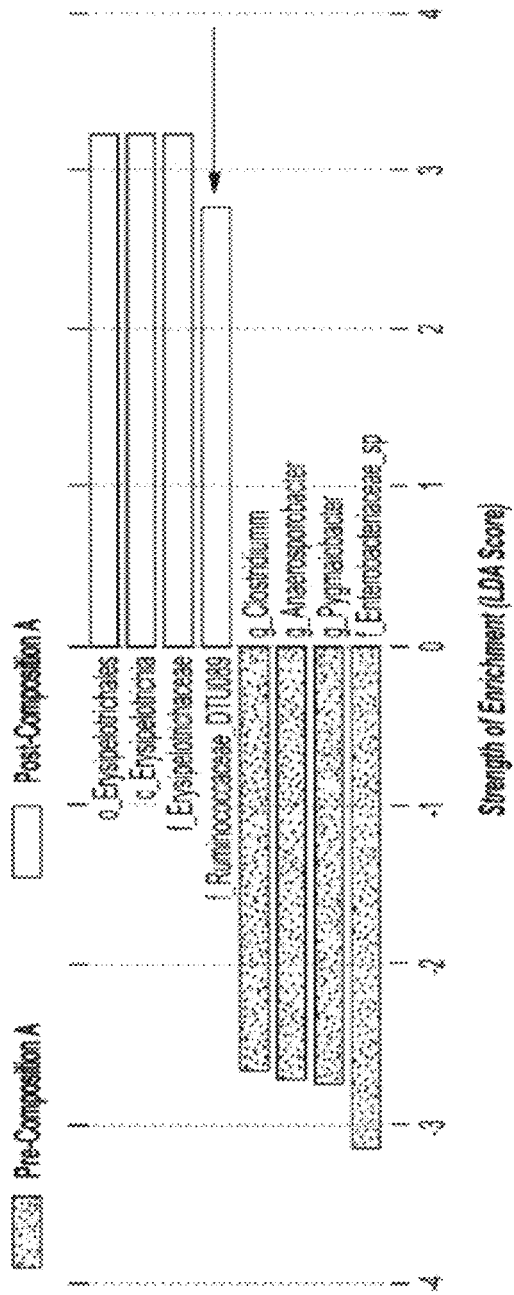
FIG. 19 is a graph showing the Strength of Enrichment (LDA Score) of observed species in the gut bacterial microbiome of subjects who were provided and consumed Composition A for 8 weeks in Example 1.

As shown in FIG. 19, the relative abundance of Candidatus, Erysipelotrichales, Erysipelotrichia, Erysipelotrichaceae, and/or Ruminococcaceae in the subject's gut was at least +2 as determined by linear discriminant analysis following at least 2 weeks of treatment with Composition A.

Figure 20:
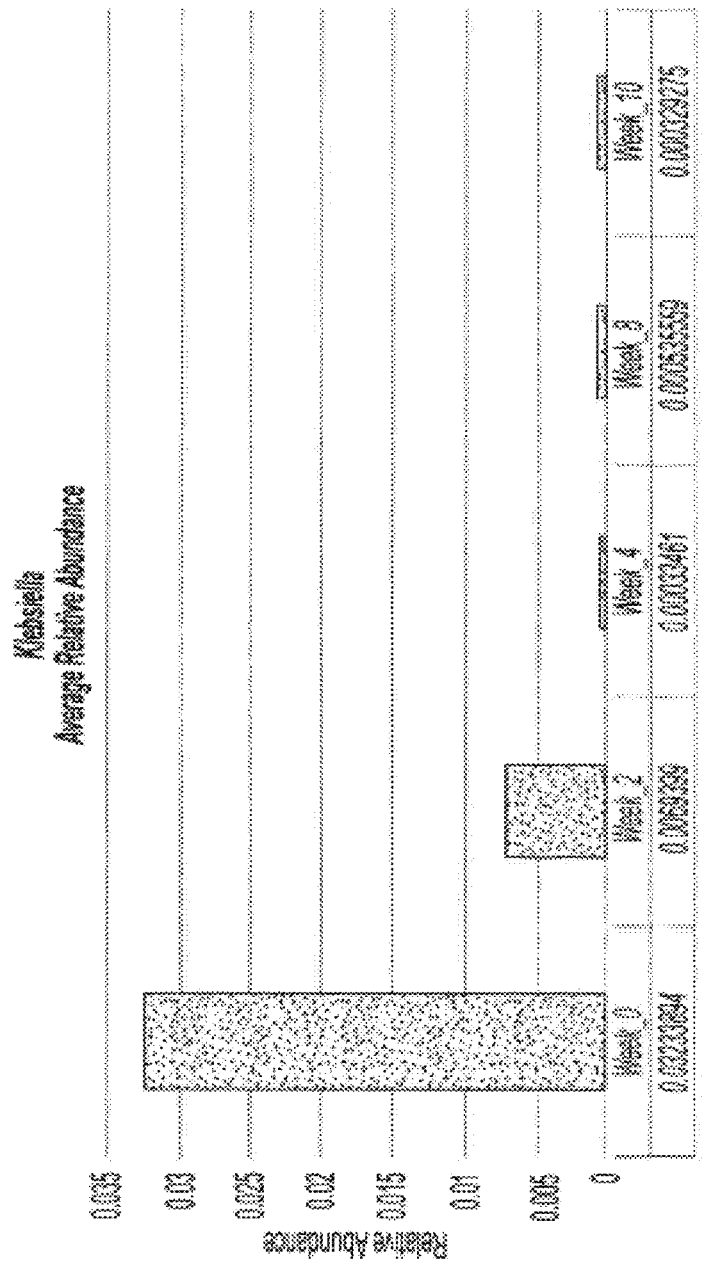
FIG. 20 is a graph showing the relative abundance of *Klebsiella* in the stool samples of subjects who were provided and consumed Composition A in Example 1.
Figure 21:
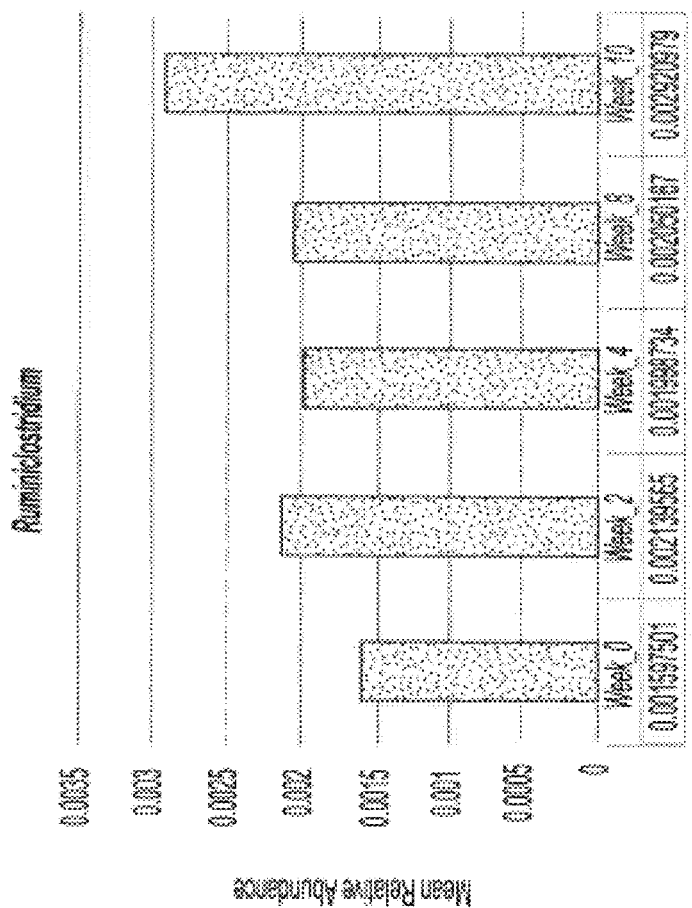
FIG. 21 is a graph showing the relative abundance of *Ruminiclostridium* in the stool samples of subjects who were provided and consumed Composition A in Example 1.
Figure 22:
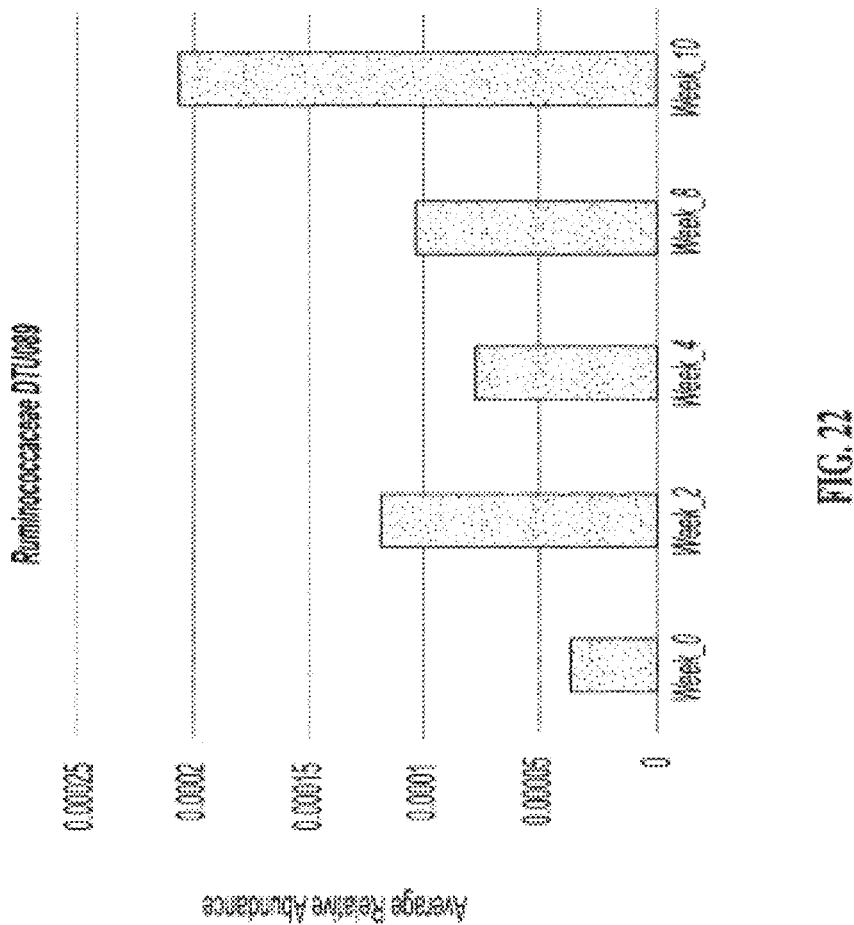
FIG. 22 is a graph showing the relative abundance of Ruminococcaceae DTU089 in the stool samples of subjects who were provided and consumed Composition A in Example 1.
Figure 23:
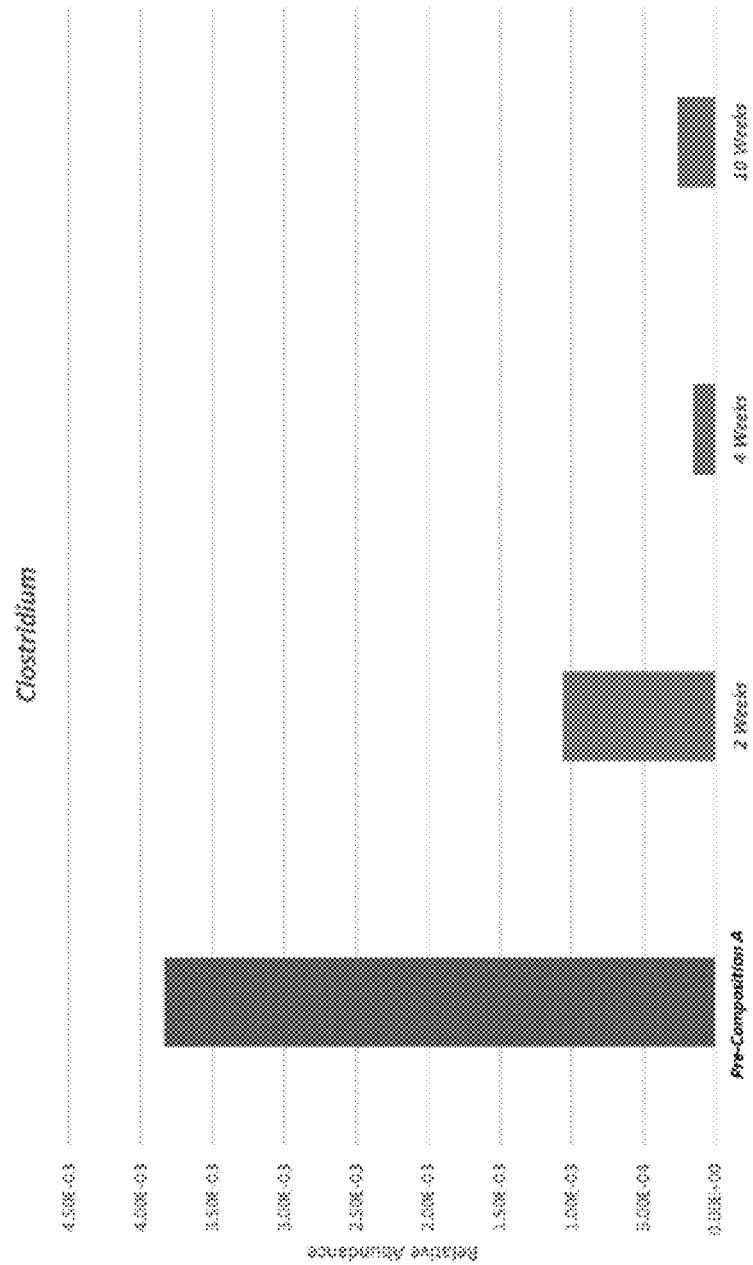
FIG. 23 is a graph showing the relative abundance of *Clostridium* in the gut bacterial microbiome of subjects who were provided and consumed Composition A in Example 1.
Figure 24:
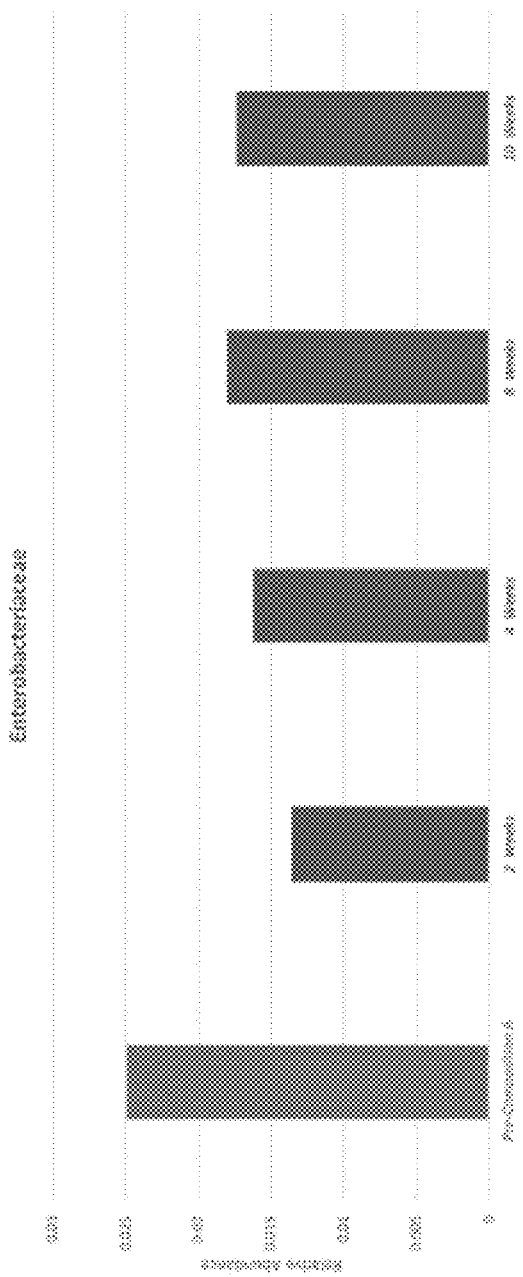
FIG. 24 is a graph showing the relative abundance of Enterobacteriaceae in the gut bacterial microbiome of subjects who were provided and consumed Composition A in Example 1.

FIG. 20 is a bar graph showing the relative abundance of Klebsiella. FIG. 21 is a bar graph showing the relative abundance of Ruminiclostridium. FIG. 22 is a bar graph showing the relative abundance of Ruminococcaceae. FIG. 23 is a bar graph showing the relative abundance of Clostridium. FIG. 24 is a bar graph showing the relative abundance of Enterobacteriaceae.

PICRUSt Plots: PICRUSt functional predictions were generated from a closed-reference OTU table generated within QIIME-1.9.0 (Langille M, Zaneveld J, Caporaso J G, McDonald D, Knights D, Reyes J, Clemente J, Burkepile D, Vega Thurber R, Knight R, Beiko R, Huttenhower C. 2013. Predictive functional profiling of microbial communities using 16S rRNA marker gene sequences. Nat Biotechnol 31:814-21). Relative abundances of level 3 summarized predicted functional genes were multiplied by 1 million and formatted as described in Segata et al. (4). Comparisons were made with "Timepoint" as the main categorical variable ("Class"). Alpha levels of 0.05 were used for both the Kruskal-Wallis and pairwise Wilcoxon tests. PICRUSt predictions were then plotted in Microsoft Excel for visualization of predicted counts per million (CPM) measures over time.

Figure 25:
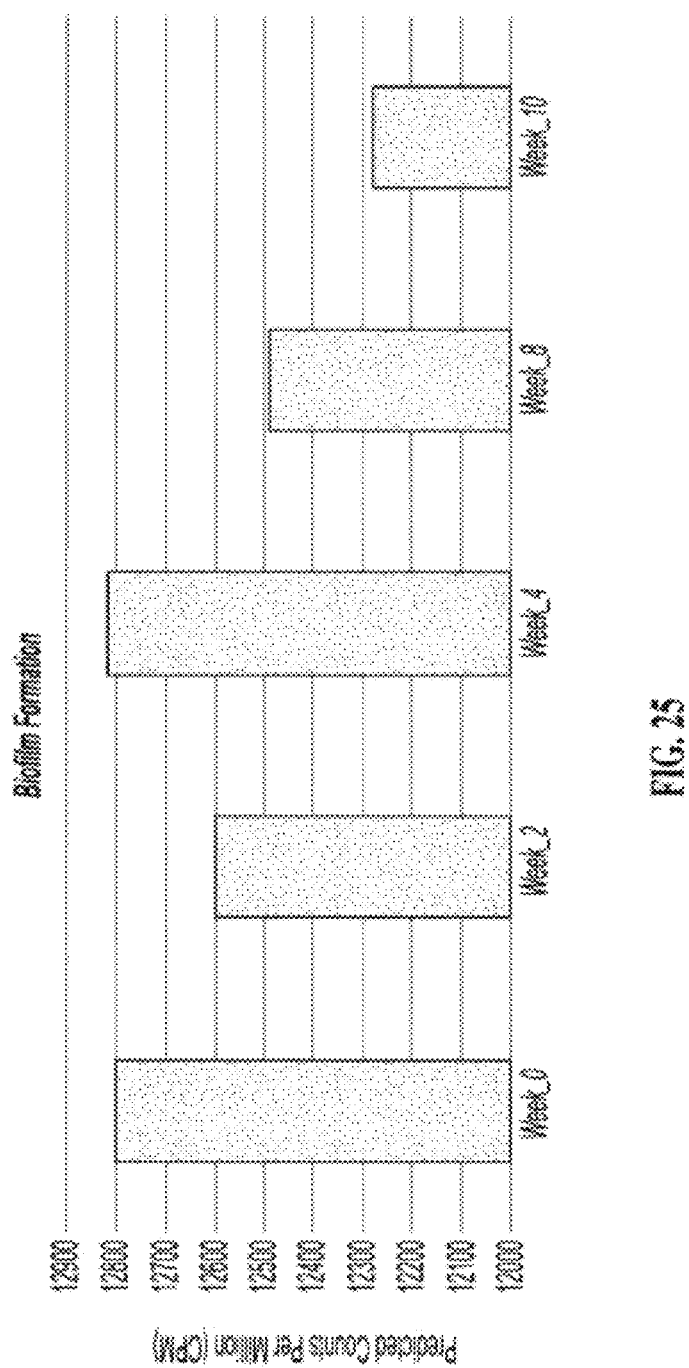
FIG. 25 is a graph showing the biofilm formation in the gut bacterial microbiome of subjects who were provided and consumed Composition A in Example 1.

As shown in FIG. 25, the biofilm formation in the subject's gut was reduced as determined by PICRUSt analysis following at least 2 weeks of treatment with Composition A.

Figure 26:
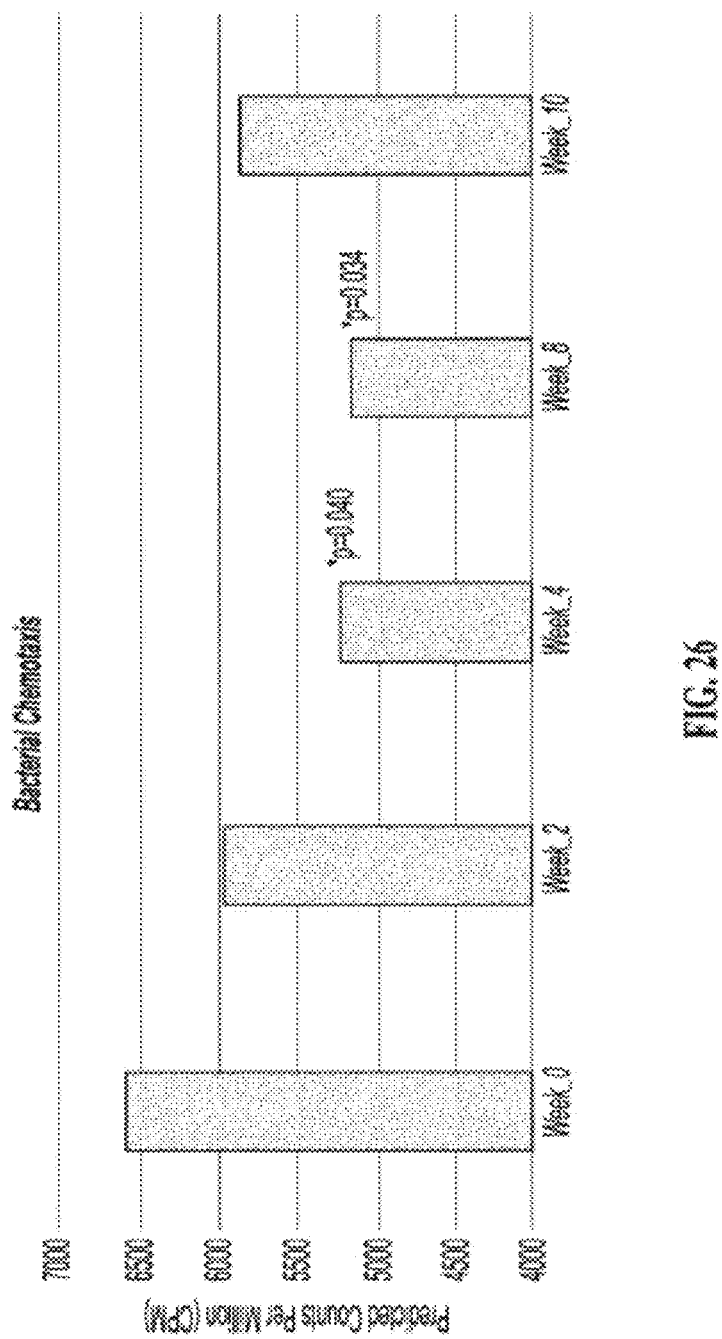
FIG. 26 is a graph showing the bacterial chemotaxis in the gut bacterial microbiome of subjects who were provided and consumed Composition A in Example 1.

As shown in FIG. 26, the predicted bacterial chemotaxis in the subject's gut was reduced as determined by PICRUSt analysis following at least 2 weeks of treatment with Composition A.

Figure 27B:
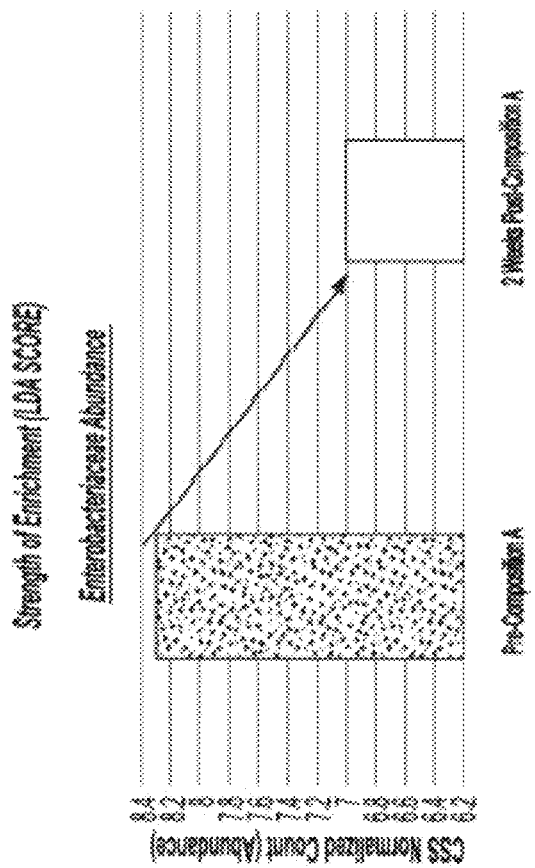
FIG. 27 shows (A) biofilm formation in the gut bacterial microbiome of subjects who were provided and consumed Composition in Example 1 and (B) abundance of Enterobacteriaceae in the gut bacterial microbiome of subjects who were provided and consumed Composition A in Example 1.
Figure 27A:
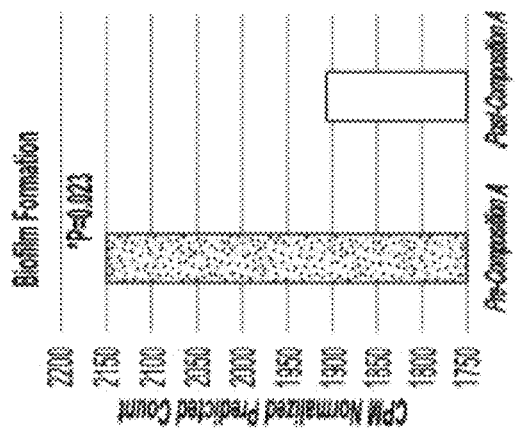

As shown in FIG. 27(A), Composition A resulted in a significant decrease in overall biofilm formation (average over the 10 weeks of the samples collected) compared to baseline. As shown in FIG. 27(B), Composition A resulted in a significant decrease in overall abundance of Enterobacteriaceae (at 2 weeks post-Composition A).

Example 2

Figure 28:
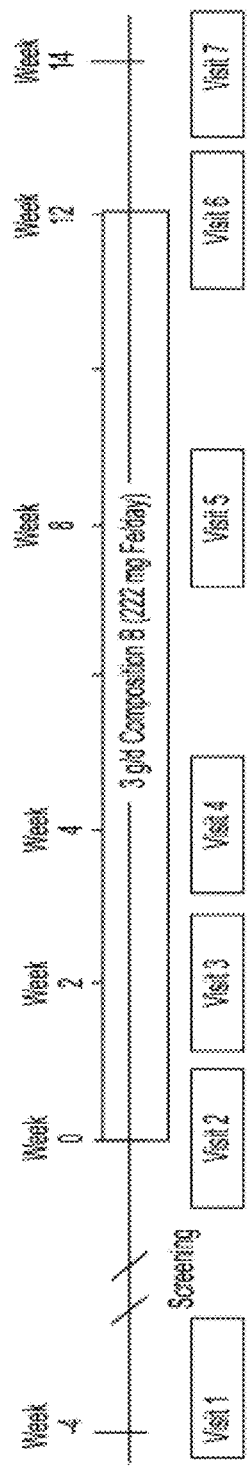
FIG. 28 is a schematic outlining the experimental protocol utilized in Example 2.

The experimental protocol is illustrated in FIG. 28. Subjects were pre-screened and only non-anemic patients (hemoglobin ≥8 g/dL) were selected to participate in the study. All subjects were instructed to stop taking iron supplements and/or multivitamins containing iron (if any) for four weeks prior to initiation of the study.

Six non-pregnant, non-postpartem female subjects with iron deficiency were instructed to take 3.0 g of Composition B/day, provided as eight 375 mg capsules, for twelve weeks. With the content being about 74 mg of iron/gram of Composition A, the intake level was 222 mg of iron per day, which is about 114% of the standard of care daily recommendation for iron salts such as ferrous sulfate (165-195 mg per day) for subject with iron deficiency.

Tolerability of Composition B was monitored by direct questioning and recording adverse events and by completion of a weekly gastrointestinal discomfort questionnaire.

Blood samples (10 mL) were drawn at screening (Week −4), baseline (Week 0), and AT Weeks 2, 4, 8, and 12 and were analyzed to measure hemoglobin levels and total iron-binding capacity (TIBC). Data are reported in FIGS. 29 and 30.

Figure 29:
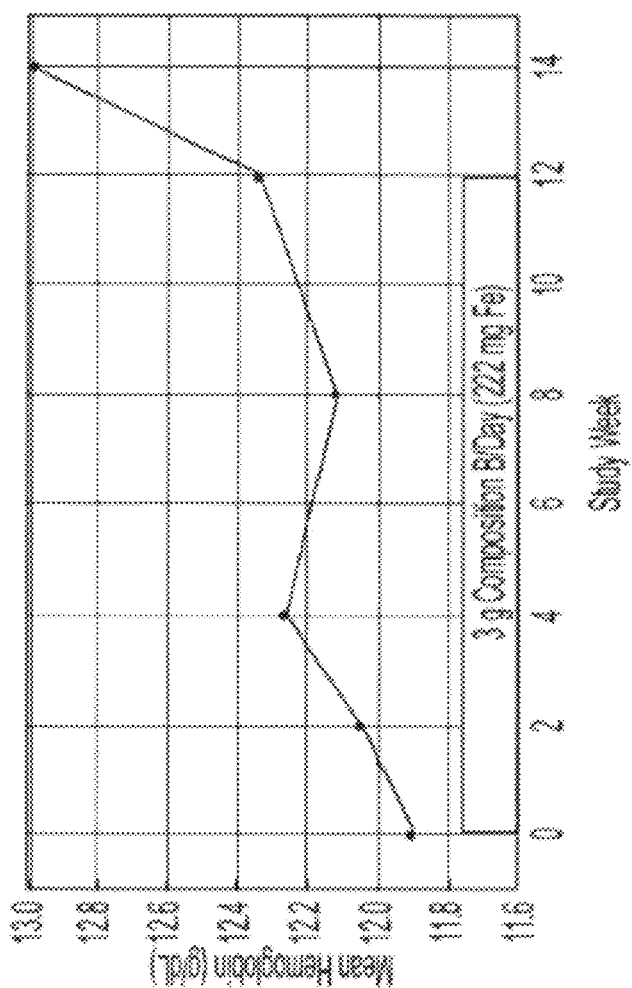
FIG. 29 is a graph reporting mean hemoglobin (g/dL) measured in subjects who were provided and consumed Composition B in Example 2.

As shown in FIG. 29, mean hemoglobin levels did not change significantly by Week 2 but did increase at Weeks 4 and 8 and remained elevated at Week 14 (two weeks following completion of the study).

Figure 30:
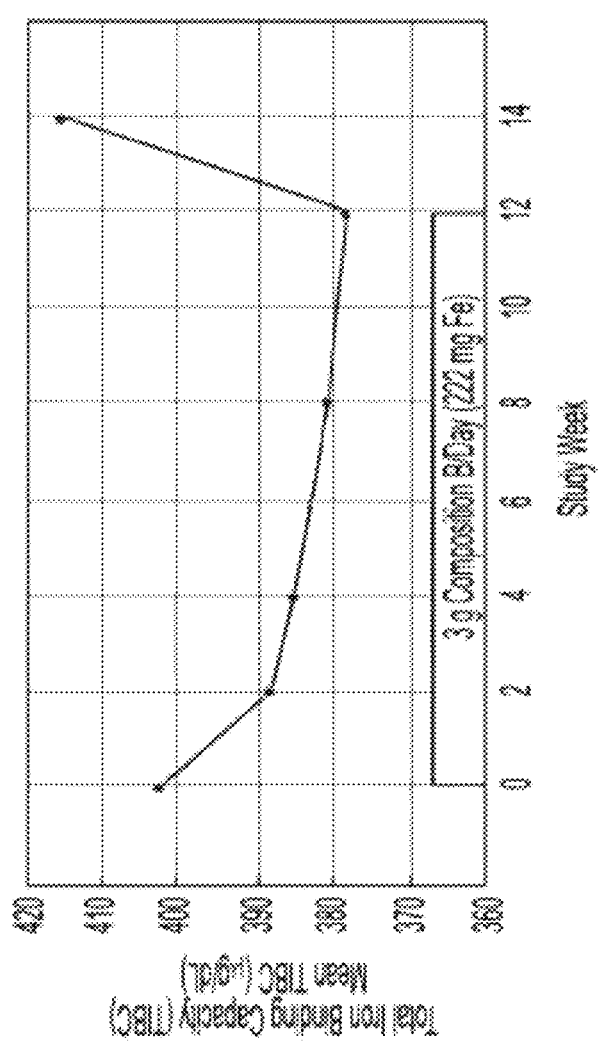
FIG. 30 is a graph reporting mean total iron binding capacity (TIBC; µg/dL) measured in subjects who were provided and consumed Composition B in Example 2.

As shown in FIG. 30, TBIC steadily decreased over the 12 weeks of the study and then increased at Week 14.

Example 3

Using a standard pre-clinical animal model of iron deficiency, we demonstrated that ferritin-expressing, iron-supplemented yeast were superior to the standard approach of administering ferrous sulfate to treat iron deficiency.

Feeding trials were performed on rats using a well-established rat model. The study was designed to directly compare the efficacy of the ferritin-enriched yeast with the standard for iron replenishment (ferrous sulfate). Twenty-day-old rats were housed 1 per cage and fed an iron-deficient diet (ID; 3 ppm iron). All rats received food and deionized distilled water ad libitum in a temperature (23±2° C.) and humidity (40%) controlled room maintained on a 12:12 hr light/dark cycle (lights on 6:00 am to 6:00 pm). The ID diet was prepared following the recipe of the American Institute of Nutrition (AIN)-93G diet with cornstarch as the sole source of carbohydrate. Iron levels of the diet were verified using atomic absorption spectrophotometry after wet digestion with nitric acid.

A total of 50 µl of blood was collected from each rat every 3-4 days after beginning the ID diet to monitor hematocrit and hemoglobin levels. After 23 days of feeding an iron-deficient diet (postnatal day 43), mean hemoglobin and hematocrit levels were approximately 102 g/dL and 34%, respectively. Rats were then randomly divided into 4 groups (n=6/group).

Each diet was prepared with the ID diet (3 ppm iron) as the base diet. Iron supplemented yeast (Composition D), iron supplemented yeast expressing ferritin (Composition C), or iron sulfate was added to the ID diet to 50 ppm to make the control diets. The rats were fed the assigned diets ad libitum, and hemoglobin and hematocrit levels were again measured every 3-4 days until postnatal day 61 (total of 17 days). Food intake was measured for the entire feeding period and was not different between groups. Rats were euthanized at P61 and hematology and brain measurements determined.

Figure 31:
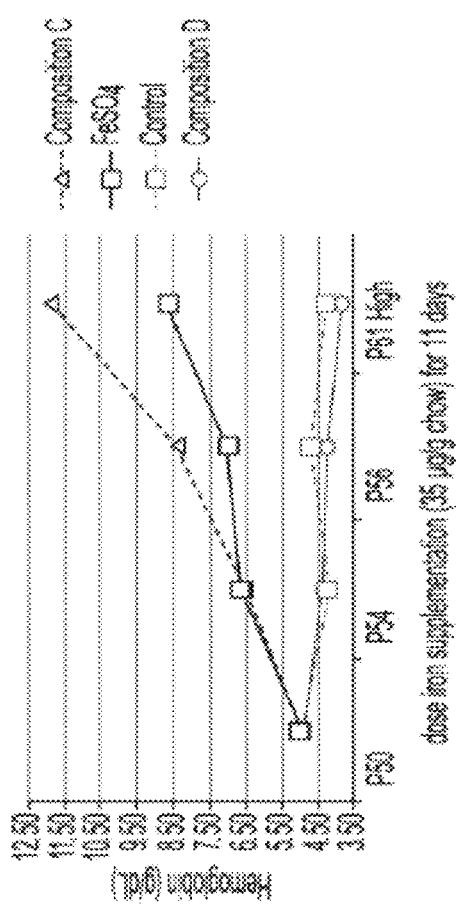
FIG. 31 is a graph showing the mean hemoglobin (g/dL) measured in subjects who were provided and consumed Composition C in Example 3.

Data are reported in FIG. 31. Rats were made iron deficient by feeding them an iron-deficient diet (3 µg/g iron) beginning at P21. When their hemoglobin levels reached ~5 g/dL, the rats were assigned to one of 4 dietary groups: 1) Composition C (H-ferritin Yeast Diet Group: Fed 35 µg iron/g as the iron source; 2) Composition D (Yeast Group: Fed yeast in the diet without iron at the same weight equivalent as the YFC group; 3) Control (Iron-deficient Group: Maintained on iron-deficient diet); 4) Ferrous Sulfate diet: standard of care group fed standard diet with ferrous sulfate (35 µg iron/g). The data in FIG. 33 show that Composition C was significantly better at recovering the hematological iron parameters than the ferrous sulfate supplement.

We claim:

1. A composition comprising (a) a microbe expressing mammalian H-ferritin or a homologue thereof and (b) elemental iron in an amount of at least 3% by weight on a dry matter basis of the microbe expressing mammalian H-ferritin or a homologue thereof and the elemental iron; wherein at least 60% of the elemental iron is complexed with the mammalian H-ferritin or the homologue thereof.

2. The composition of claim 1, wherein the mammalian H-ferritin is human H-ferritin or a homologue thereof.

3. The composition of claim 1, wherein the homologue has at least 80% sequence identity with human H-ferritin.

4. The composition of claim 1, wherein a source of the elemental iron is an iron salt, an organic iron complex, an elemental iron nanoparticle, or combinations thereof.

5. The composition of claim 1, wherein the microbe comprises a fungus, an algae, a bacterium, a protozoan, a virus, a microscopic helminth, a microorganism, a lichen, or combinations thereof.

6. The composition of claim 1, further comprising at least one filler.

7. The composition of claim 1, consisting essentially of (a) the microbe expressing mammalian H-ferritin or a homologue thereof and (b) the elemental iron in an amount of at least 3% by weight based on dry weight of the microbe expressing H-ferritin and the elemental iron.

8. The composition of claim 1, wherein the microbe further comprises intracellular elemental iron that is not complexed with the mammalian H-ferritin or the homologue thereof.

9. The composition of claim 1, further comprising a second microbe, a probiotic, a prebiotic, or combinations thereof.

10. The composition of claim 9, wherein the second microbe does not express ferritin.

11. An ingestible item comprising the composition of claim 1.

12. The ingestible item of claim 11, wherein the ingestible item is in the form of a medical food, a food, a food ingredient, or combinations thereof.

13. A dietary supplement comprising the composition of claim 1.

14. A pharmaceutical composition comprising the composition of claim 1.

15. A method for treating a subject comprising administering to the subject a composition comprising (a) a microbe expressing mammalian H-ferritin or a homologue thereof and (b) elemental iron in an amount of at least 3% by weight on a dry matter basis of the microbe expressing mammalian H-ferritin or a homologue thereof and the elemental iron.

16. The method of claim 15, wherein at least 60% of the elemental iron is complexed with the mammalian H-ferritin or a homologue thereof.

17. The method of claim 15, wherein the composition comprises at least 13 mg of elemental iron.

18. The method of claim 15, wherein the administering comprises a single dose.

19. The method of claim 15, wherein the administering comprises more than one dose administered sequentially.

20. The method of claim 15, wherein at least 1 week following the administering:
(a) the average observed bacterial species richness in the subject's gut is substantially the same as the average observed bacterial species richness in the subject's gut prior to the administering;
(b) the relative abundance of *Klebsiella*, Enterobacteriales, Enterobacteriaceae, *Clostridium*, Anaerosporobacter, and/or Pygmaiobacter in the subject's gut is at least −2 as determined by linear discriminant analysis;
(c) the relative abundance of *Candidatus*, Erysipelotrichales, Erysipelotrichia, Erysipelotrichaceae, and/or Ruminococcaceae in the subject's gut is at least +2 as determined by linear discriminant analysis;
(d) the level of biofilm formation in the subject's gut as determined by PICRUSt analysis is reduced by at least 1% relative to levels prior to the administering;
(e) the level of biofilm formation in the subject's gut as determined by PICRUSt analysis is reduced by at least 50 cpm compared to levels prior to the administering;
(f) the predicted bacterial chemotaxis in the subject's gut as determined by PICRUSt analysis is reduced by at least 1% relative to levels prior to the administering;
(g) the predicted bacterial chemotaxis in the subject's gut as determined by PICRUSt analysis is reduced by at least 200 cpm compared to the predicted cpm prior to the administering;
(h) the subject's hemoglobin concentration is increased by at least 1% relative to the hemoglobin concentration prior to the administering;
(i) the subject's hemoglobin concentration is increased by at least 0.1 g/dL relative to the hemoglobin concentration prior to the administering;
(j) the subject's total iron binding capacity is decreased by at least 2.5% relative to the total iron binding capacity prior to the administering;
(k) the subject's total iron binding capacity is decreased by at least 40 µg/dL relative to the total iron binding capacity prior to the administering;
(l) the subject's FACIT Fatigue Score is increased by at least 5 points relative to the FACIT Fatigue Score prior to the administering;
(m) the subject's SF-36 Bodily Pain Score is increased by at least 5 points relative to the SF-36 Bodily Pain Score prior to the administering;
(n) the subject's SF-36 Vitality Score is increased by at least 5 points relative to the SF-36 Vitality Score prior to the administering; and/or
(o) the mean incidence of the subject's gastrointestinal symptoms per week are less than a two-fold increase relative to the mean incidence of the subject's gastrointestinal symptoms per week prior to the administering.

21. The method of claim 20, wherein the administering comprises an average of at least 13 mg of elemental iron per day.

22. The method of claim 15, further comprising dietary management.

23. The method of claim 15, wherein the subject is not iron deficient.

24. A method of altering the composition of the gut bacterial microbiome in a subject, the method comprising administering to the subject a composition comprising (a) a microbe expressing mammalian H-ferritin or a homologue thereof and (b) elemental iron in an amount of at least 3% by weight on a dry matter basis of the microbe expressing mammalian H-ferritin or a homologue thereof and the elemental iron.

25. The method of claim 24, wherein at least 60% of the elemental iron is complexed with the mammalian H-ferritin or the homologue thereof.

26. The method of claim 24, wherein at least 1 week following the administering:
(a) the average observed bacterial species richness in the subject's gut is substantially the same as the average observed bacterial species richness in the subject's gut prior to the administering;
(b) the relative abundance of *Klebsiella*, Enterobacteriales, Enterobacteriaceae, *Clostridium*, Anaerosporobacter, and/or Pygmaiobacter in the subject's gut is at least −2 as determined by linear discriminant analysis;
(c) the relative abundance of *Candidatus*, Erysipelotrichales, Erysipelotrichia, Erysipelotrichaceae, and/or Ruminococcaceae in the subject's gut is at least +2 as determined by linear discriminant analysis;
(d) the level of biofilm formation in the subject's gut as determined by PICRUSt analysis is reduced by at least 1% relative to levels prior to the administering;
(e) the level of biofilm formation in the subject's gut as determined by PICRUSt analysis is reduced by at least 50 cpm compared to levels prior to the administering;
(f) the predicted bacterial chemotaxis in the subject's gut as determined by PICRUSt analysis is reduced by at least 1% relative to levels prior to the administering;
(g) the predicted bacterial chemotaxis in the subject's gut as determined by PICRUSt analysis is reduced by at least 200 cpm compared to the predicted cpm prior to the administering;
(h) the subject's hemoglobin concentration is increased by at least 1% relative to the hemoglobin concentration prior to the administering;
(i) the subject's hemoglobin concentration is increased by at least 0.1 g/dL relative to the hemoglobin concentration prior to the administering;
(j) the subject's total iron binding capacity is decreased by at least 2.5% relative to the total iron binding capacity prior to the administering;
(k) the subject's total iron binding capacity is decreased by at least 40 µg/dL relative to the total iron binding capacity prior to the administering;
(l) the subject's FACIT Fatigue Score is increased by at least 5 points relative to the FACIT Fatigue Score prior to the administering;
(m) the subject's SF-36 Bodily Pain Score is increased by at least 5 points relative to the SF-36 Bodily Pain Score prior to the administering;
(n) the subject's SF-36 Vitality Score is increased by at least 5 points relative to the SF-36 Vitality Score prior to the administering; and/or
(o) the mean incidence of the subject's gastrointestinal symptoms per week are less than a two-fold increase relative to the mean incidence of the subject's gastrointestinal symptoms per week prior to the administering.

27. The method of claim 26, wherein the administering comprises an average of at least 13 mg of elemental iron per day.

28. The method of claim 24, further comprising dietary management.

* * * * *